(12) United States Patent
Creutz et al.

(10) Patent No.: US 10,406,092 B2
(45) Date of Patent: Sep. 10, 2019

(54) METHOD FOR PRODUCING TRANSPARENT OR SEMI-TRANSPARENT LIQUID GLYCERIN-DERIVATIVE-MODIFIED SILICONE COMPOSITION

(71) Applicants: Dow Corning Toray Co., Ltd., Tokyo (JP); Dow Corning Corporation, Midland, MI (US)

(72) Inventors: Serge Creutz, Seneffe (BE); Seiki Tamura, Ichihara (JP); Sayuri Sawayama, Ichihara (JP); Seiji Hori, Sabae (JP)

(73) Assignees: DOW SILICONES CORPORATION, Midland, MI (US); DOW CORNING TORAY CO., LTD., Tokyo (JP)

(*) Notice: Subject to any disclaimer, the term of this patent is extended or adjusted under 35 U.S.C. 154(b) by 0 days.

(21) Appl. No.: 14/655,160

(22) PCT Filed: Dec. 26, 2013

(86) PCT No.: PCT/JP2013/085007
§ 371 (c)(1),
(2) Date: Sep. 25, 2015

(87) PCT Pub. No.: WO2014/104258
PCT Pub. Date: Jul. 3, 2014

(65) Prior Publication Data
US 2016/0008260 A1    Jan. 14, 2016

(30) Foreign Application Priority Data
Dec. 28, 2012 (JP) ................... 2012-288071

(51) Int. Cl.
| A61K 8/892 | (2006.01) |
| A61K 8/894 | (2006.01) |
| C08G 77/14 | (2006.01) |
| A61Q 19/00 | (2006.01) |
| A61K 8/92 | (2006.01) |
| A61Q 1/02 | (2006.01) |

(52) U.S. Cl.
CPC .............. *A61K 8/892* (2013.01); *A61K 8/894* (2013.01); *A61K 8/92* (2013.01); *A61Q 1/02* (2013.01); *A61Q 19/00* (2013.01); *C08G 77/14* (2013.01); *A61K 2800/10* (2013.01); *A61K 2800/262* (2013.01)

(58) Field of Classification Search
None
See application file for complete search history.

(56) References Cited

U.S. PATENT DOCUMENTS

| 4,431,789 A | 2/1984 | Okazaki et al. |
| 4,515,979 A | 5/1985 | Otsuki et al. |
| 4,616,076 A | 10/1986 | Ona et al. |
| 4,631,208 A | 12/1986 | Westall |
| 4,698,178 A | 10/1987 | Huttinger et al. |
| 5,144,054 A | 9/1992 | Shioya et al. |
| 5,225,509 A | 7/1993 | Heinrich et al. |
| 5,260,402 A | 11/1993 | Weitemeyer et al. |
| 5,288,831 A | 2/1994 | Ichinohe et al. |
| 5,306,838 A | 4/1994 | Shioya et al. |
| 5,466,849 A | 11/1995 | Shioya et al. |
| 5,472,686 A | 12/1995 | Tsubaki et al. |
| 5,484,950 A | 1/1996 | Crivello |
| 5,609,167 A | 3/1997 | Hensen et al. |
| 5,654,362 A | 8/1997 | Schulz, Jr. et al. |
| 5,656,200 A | 8/1997 | Boettcher et al. |
| 5,660,819 A | 8/1997 | Tsubaki et al. |
| 5,874,069 A | 2/1999 | Mendolia et al. |
| 5,889,108 A | 3/1999 | Zhang |
| 5,919,441 A | 7/1999 | Mendolia et al. |
| 5,929,163 A | 7/1999 | Harashima |
| 5,981,680 A | 11/1999 | Petroff et al. |
| 6,043,203 A | 3/2000 | Urfer et al. |
| 6,150,311 A | 11/2000 | Decoster et al. |
| 6,168,782 B1 | 1/2001 | Lin et al. |
| 6,184,407 B1 | 2/2001 | Yoshitake et al. |
| 6,280,748 B1 | 8/2001 | Morita et al. |
| 6,534,072 B2 | 3/2003 | Mondet et al. |
| 6,576,623 B1 | 6/2003 | Nakanishi et al. |
| 6,660,281 B1 | 12/2003 | Nakanishi et al. |
| 7,001,971 B2 | 2/2006 | Nakanishi |

(Continued)

FOREIGN PATENT DOCUMENTS

| CA | 2291284 A1 | 5/2000 |
| CN | 102257040 A | 11/2011 |

(Continued)

OTHER PUBLICATIONS

International Search Report for Application No. PCT/JP2013/085007 dated Apr. 1, 2014, 5 pages.
English language abstract for CN 102257040 extracted from espacenet.com database on Oct. 1, 2015, 1 page.
English language abstract for CN 102257041 extracted from espacenet.com database on Oct. 1, 2015, 2 pages.
English language abstract for CN 102639605 extracted from espacenet.com database on Oct. 1, 2015, 1 page.
English language abstract for JPS 57-149290 extracted from espacenet.com database on Oct. 1, 2015, 2 pages.
English language abstract for JPS 62-34039 extracted from espacenet.com database on Oct. 1, 2015, 2 pages.

(Continued)

*Primary Examiner* — Craig D Ricci
(74) *Attorney, Agent, or Firm* — Howard & Howard Attorneys PLLC

(57) ABSTRACT

The present invention relates to a method for producing a transparent or semi-transparent liquid glycerin derivative-modified silicone composition that comprises a hydration step of adding water to a liquid glycerin derivative-modified silicone or composition thereof. The present invention can provide a liquid glycerin derivative-modified silicone composition having a transparent or semi-transparent appearance can be provided.

15 Claims, No Drawings

(56) References Cited

U.S. PATENT DOCUMENTS

| | | |
|---|---|---|
| 7,482,419 B2 | 1/2009 | Caprasse et al. |
| 7,507,775 B2 | 3/2009 | Leatherman et al. |
| 7,601,680 B2 | 10/2009 | Wang et al. |
| 7,612,051 B2 | 11/2009 | Kamei et al. |
| 7,655,744 B2 | 2/2010 | Miyanaga |
| 7,771,709 B2 | 8/2010 | Nakanishi et al. |
| 7,994,250 B2 | 8/2011 | Origuchi et al. |
| 7,998,903 B2 | 8/2011 | Nakanishi et al. |
| 8,034,891 B2 | 10/2011 | Okawa |
| 8,080,239 B2 | 12/2011 | Matsuo et al. |
| 8,513,174 B2 | 8/2013 | Araki et al. |
| 8,597,619 B2 | 12/2013 | Tamura et al. |
| 8,686,174 B2 | 4/2014 | Okawa |
| 8,715,626 B2 | 5/2014 | Tamura et al. |
| 8,784,787 B2 | 7/2014 | Tamura et al. |
| 8,877,886 B2 | 11/2014 | Souda et al. |
| 9,133,309 B2 | 9/2015 | Iimura et al. |
| 9,580,600 B2 | 2/2017 | Tamura et al. |
| 9,585,832 B2 | 3/2017 | Tamura et al. |
| 9,688,821 B2 | 6/2017 | Tamura et al. |
| 2002/0131947 A1 | 9/2002 | Nakanishi |
| 2003/0158363 A1 | 8/2003 | Nakanishi |
| 2004/0091439 A1 | 5/2004 | Kamei et al. |
| 2004/0253197 A1 | 12/2004 | Sakuta |
| 2005/0008600 A1 | 1/2005 | Nakanishi et al. |
| 2005/0261133 A1* | 11/2005 | Nakanishi ............... C08G 77/38 504/358 |
| 2006/0013843 A1 | 1/2006 | Shimizu et al. |
| 2006/0018935 A1 | 1/2006 | Nishijima et al. |
| 2006/0034875 A1 | 2/2006 | Nakanishi et al. |
| 2007/0207176 A1 | 9/2007 | Kamei et al. |
| 2009/0203802 A1 | 8/2009 | Kamei et al. |
| 2009/0238781 A1 | 9/2009 | Sakuta et al. |
| 2009/0326151 A1 | 12/2009 | Shimizu et al. |
| 2010/0190871 A1 | 7/2010 | Araki et al. |
| 2011/0182846 A1 | 7/2011 | Ikeda et al. |
| 2011/0251417 A1 | 10/2011 | Okawa |
| 2012/0035275 A1 | 2/2012 | Kojima et al. |
| 2012/0245305 A1 | 9/2012 | Souda et al. |
| 2012/0269747 A1 | 10/2012 | Iimura et al. |
| 2012/0269748 A1 | 10/2012 | Tamura et al. |
| 2012/0269875 A1 | 10/2012 | Tamura et al. |

FOREIGN PATENT DOCUMENTS

| | | |
|---|---|---|
| CN | 102257041 A | 11/2011 |
| CN | 102639605 A | 8/2012 |
| EP | 1031592 A2 | 8/2000 |
| EP | 2014701 A2 | 1/2009 |
| EP | 2 103 301 A1 | 9/2009 |
| EP | 2174985 A1 | 4/2010 |
| EP | 2180028 A1 | 4/2010 |
| EP | 2492300 A1 | 8/2012 |
| JP | 50004199 | 1/1975 |
| JP | S5541210 B2 | 10/1980 |
| JP | 57139123 | 8/1982 |
| JP | S 57-149290 A | 9/1982 |
| JP | S6018525 | 1/1985 |
| JP | 61090732 | 5/1986 |
| JP | 61123635 | 6/1986 |
| JP | 61127733 | 6/1986 |
| JP | 61293903 | 12/1986 |
| JP | 61293904 | 12/1986 |
| JP | S 62-34039 A | 7/1987 |
| JP | 62187406 | 8/1987 |
| JP | S 62-195389 A | 8/1987 |
| JP | 62215510 | 9/1987 |
| JP | 62216635 | 9/1987 |
| JP | H02302438 A | 12/1990 |
| JP | H 05-186596 A | 1/1992 |
| JP | H 04-108795 A | 4/1992 |
| JP | 04211605 | 8/1992 |
| JP | 04234307 | 8/1992 |
| JP | 05112424 | 5/1993 |
| JP | 05163436 | 6/1993 |
| JP | 05311076 | 11/1993 |
| JP | 06157236 | 6/1994 |
| JP | 06305933 | 11/1994 |
| JP | H 06-089147 B | 11/1994 |
| JP | 07025728 | 1/1995 |
| JP | 07033622 | 2/1995 |
| JP | 07100358 | 4/1995 |
| JP | 07187945 | 7/1995 |
| JP | H07330907 | 12/1995 |
| JP | 08217626 | 8/1996 |
| JP | 08268831 | 10/1996 |
| JP | 08268832 | 10/1996 |
| JP | 02583412 | 2/1997 |
| JP | 09071504 | 3/1997 |
| JP | 2613124 | 5/1997 |
| JP | H09165315 | 6/1997 |
| JP | H09165318 | 6/1997 |
| JP | 09194323 | 7/1997 |
| JP | H 09-194594 A | 7/1997 |
| JP | 02719303 | 2/1998 |
| JP | 10167946 | 6/1998 |
| JP | 10245317 | 9/1998 |
| JP | 10310504 | 11/1998 |
| JP | 10310505 | 11/1998 |
| JP | 10310506 | 11/1998 |
| JP | 10310507 | 11/1998 |
| JP | 10310508 | 11/1998 |
| JP | 10310509 | 11/1998 |
| JP | 10316536 | 12/1998 |
| JP | 2844453 | 1/1999 |
| JP | 11049957 | 2/1999 |
| JP | 2000063225 A | 2/2000 |
| JP | 2000072784 A | 3/2000 |
| JP | 2000128740 A | 5/2000 |
| JP | 2000143458 A | 5/2000 |
| JP | 2000239390 A | 9/2000 |
| JP | 2001011281 A | 1/2001 |
| JP | 2001039819 A | 2/2001 |
| JP | 2001072891 A | 3/2001 |
| JP | 2001316473 A | 11/2001 |
| JP | 2002038013 A | 2/2002 |
| JP | 2002-179798 A | 6/2002 |
| JP | 2002179797 A | 6/2002 |
| JP | 2004169015 A | 6/2004 |
| JP | 2004182680 A | 7/2004 |
| JP | 2004231608 A | 8/2004 |
| JP | 2004-339244 A | 12/2004 |
| JP | 2005-042097 A | 2/2005 |
| JP | 2005-089494 A | 4/2005 |
| JP | 2005120293 | 5/2005 |
| JP | 2005194523 A | 7/2005 |
| JP | 2005330221 A | 12/2005 |
| JP | 2005344076 A | 12/2005 |
| JP | 2006218472 A | 8/2006 |
| JP | 2007532754 A | 11/2007 |
| JP | 4108795 B2 | 6/2008 |
| JP | 4134013 B2 | 8/2008 |
| JP | 2009511710 A | 3/2009 |
| JP | 2009511712 A | 3/2009 |
| JP | 2009-256616 A | 11/2009 |
| JP | 2010-144156 A | 7/2010 |
| JP | 2010-144157 A | 7/2010 |
| JP | 2011-116902 A | 6/2011 |
| JP | 2012-046507 A | 3/2012 |
| JP | 5541210 B2 | 7/2014 |
| KR | 2011-0087330 A | 8/2011 |
| KR | 2011-0094080 A | 8/2011 |
| KR | 2012-0117812 A | 10/2012 |
| WO | 9310748 A1 | 6/1993 |
| WO | 9406899 A1 | 3/1994 |
| WO | 9416677 A1 | 8/1994 |
| WO | 02055588 | 7/2002 |
| WO | 03041664 A1 | 5/2003 |
| WO | 03075864 A1 | 9/2003 |
| WO | 2004046226 | 6/2004 |
| WO | 2005054341 A1 | 6/2005 |
| WO | 2007135771 A1 | 11/2007 |
| WO | 2008004502 A1 | 1/2008 |

(56) References Cited

FOREIGN PATENT DOCUMENTS

| WO | 2009022621 A1 | 2/2009 |
| WO | 2009025146 A1 | 2/2009 |
| WO | WO 2010/074296 A1 | 7/2010 |
| WO | WO 2010/074297 A1 | 7/2010 |
| WO | WO 2011/049246 A1 | 4/2011 |
| WO | WO 2011/049247 A1 | 4/2011 |
| WO | WO 2011/049248 A1 | 4/2011 |
| WO | WO 2011/068251 A1 | 6/2011 |
| WO | 2012165228 A1 | 12/2012 |
| WO | 2012165237 A1 | 12/2012 |

OTHER PUBLICATIONS

English language abstract and machine-assisted English translation for JPS 62-195389 extracted from the PAJ database on Jul. 1, 2015, 6 pages.

English language abstract and machine-assisted English translation for JPH 04-108795 extracted from the PAJ database on Jul. 29, 2015, 24 pages.

English language abstract and machine-assisted English translation for JPH 05-186596 extracted from the PAJ database on Jul. 29, 2015, 19 pages.

Machine-assisted English translation for JPH 06-089147 extracted from the PAJ database on Jul. 27, 2015, 13 pages.

English language abstract and machine-assisted English translation for JPH 09-194594 extracted from the PAJ database on Jul. 29, 2015, 16 pages.

English language abstract for JP 2002-179798 extracted from espacenet.com database on Oct. 1, 2015, 2 pages.

English language abstract and machine-assisted English translation for JP 2004-339244 extracted from the PAJ database on Jul. 28, 2015, 29 pages.

English language abstract for JP 2005-042097 extracted from espacenet.com database on Oct. 1, 2015, 2 pages.

English language abstract and machine-assisted English translation for JP 2005-089494 extracted from the PAJ database on Jul. 28, 2015, 12 pages.

English language abstract for JP 2009-256616 extracted from espacenet.com database on Oct. 1, 2015, 2 pages.

English language abstract for JP 2010-144156 extracted from espacenet.com database on Oct. 1, 2015, 1 page.

English language abstract for JP 2010-144157 extracted from espacenet.com database on Oct. 1, 2015, 2 pages.

English language abstract for JP 2011-116902 extracted from espacenet.com database on Oct. 1, 2015, 2 pages.

English language abstract for JP 2012-046507 extracted from espacenet.com database on Oct. 1, 2015, 1 page.

English language abstract for KR 2011-0087330 extracted from espacenet.com database on Oct. 1, 2015, 1 page.

English language abstract for KR 2011-0094080 extracted from espacenet.com database on Oct. 1, 2015, 2 pages.

English language abstract for KR 2012-0117812 extracted from espacenet.com database on Oct. 1, 2015, 1 page.

English language abstract for WO 2011/049246 extracted from espacenet.com database on Oct. 1, 2015, 2 pages.

English language abstract for WO 2011/049247 extracted from espacenet.com database on Oct. 1, 2015, 2 pages.

English language abstract for WO 2011/049248 extracted from espacenet.com database on Oct. 1, 2015, 2 pages.

English language abstract for JP 2001-011281 extracted from the espacenet.com database on Jul. 16, 2012, 14 pages.

English language abstract for JP 2001-039819 extracted from the espacenet.com database on Jul. 17, 2012, 29 pages.

English language abstract for JP 2001-072891 extracted from the espacenet.com database on Jul. 17, 2012, 23 pages.

English language abstract for JP 2002-038013 extracted from the espacenet.com database on Jul. 16, 2012, 19 pages.

English language abstract for JP 2004-169015 extracted from espacenet.com database on Jul. 16, 2012, 43 pages.

English language abstract for JP 2005-344076 extracted from the espacenet.com database on Jul. 26, 2012, 18 pages.

English language abstract for JP 2006-218472 extracted from the espacenet.com database on Nov. 26, 2012, 14 pages.

English language abstract for JP 4108795 extracted from the espacenet.com database on Nov. 26, 2012, 21 pages.

English language abstract for JP 4134013 extracted from the espacenet.com database on Nov. 26, 2012, 19 pages.

English language abstract for JP 61-127733 extracted from the espacenet.com database on Jul. 26, 2012, 12 pages.

English language abstract and machine-assisted English translation for JPS 61-293903 extracted from espacenet.com database on Nov. 4, 2017, 7 pages.

English language abstract and machine-assisted English language translation for JPS 61-293904 extracted from espacenet.com database on Nov. 4, 2017, 9 pages.

English language abstract for JP 62-034039 extracted from the espacenet.com database on Nov. 26, 2012, 14 pages.

English language abstract and machine-assisted English translation for JPS 62-187406 extracted from the espacenet.com database on Nov. 4, 2017, 8 pages.

English language abstract and machine-assisted English translation for JPS 62-215510 extracted from espacenet.com database on Nov. 4, 2017, 8 pages.

English language abstract and machine-assisted English translation for JPS 62-216635 extracted from espacenet.com database on Nov. 4, 2017, 11 pages.

English language abstract for JP2005042097 extracted from espacenet.com database on Sep. 9, 2014, 2 pages. Also see English Equivalent US2005/0008600.

English language abstract for JP2613124 extracted from espacenet.com database on Sep. 9, 2014, 2 pages. Machine-assisted English translation extracted from PAJ database on Aug. 27, 2014, 43 pages.

English language abstract for JPH02302438 extracted from espacenet.com database on Sep. 9, 2014, 1 page. Also see English equivalent U.S. Pat. No. 5,288,831.

English language abstract for JPS57149290 extracted from espacenet.com database on Sep. 8, 2014, 2 pages. Also see English equivalent U.S. Pat. No. 4,431,789.

English language abstract for JPS6018525 extracted from espacenet.com database on Sep. 9, 2014, 2 pages. Also see English equivalent U.S. Pat. No. 4,515,979.

English language abstract for JPS62195389 extracted from espacenet.com database on Sep. 8, 2014, 2 pages.

English language abstract and machine-assisted English translation of equivalent JP 3678420 for WO 03/041664 extracted from the espacenet.com database on Jul. 26, 2012, 27 pages.

English language abstract and machine-assisted English translaton of equivalent JP 3625471 for WO 03/075864 extracted from the espacenet.com database on Jul. 16, 2012, 17 pages.

English language abstract for WO 2007/135771 extracted from the espacenet.com database on Jul. 17, 2012, 160 pages.

English language abstract for WO 2009/022621 extracted from the espacenet.com database on Jul. 26, 2012, 53 pages.

English language abstract for WO 2009/025146 extracted from the espacenet.com database on Jul. 26, 2012, 48 pages.

English language abstract for WO02055588 extracted from espacenet.com database on Sep. 9, 2014, 2 pages. Also see English equivalent US2003/0158363.

English language abstract for WO2004046226 extracted from espacenet.com database on Sep. 9, 2014, 2 pages. Also see English equivalent US 2006/0018935.

English language abstract not available for JP 2007-532754; however, see English equivalent U.S. Pat. No. 7,482,419. Original document extracted from espacenet.com database on Jul. 16, 2012, 39 pages.

English language abstract not available for JP 2009-511710; however, see English equivalent U.S. Pat. No. 7,507,775. Orginal document extracted from the espacenet.com database on Jul. 26, 2012, 29 pages.

(56) References Cited

OTHER PUBLICATIONS

English language abstract not available for JP 2009-511712; however, see English equivalent U.S. Pat. No. 7,601,680, Original document extracted from the espacenet.com database on Jul. 26, 2012, 29 pages.
Machine-assisted English language abstract for JPS 61-090732 extracted from espacenet.com database on Nov. 4, 2017, 3 pages.
English language abstract not available for JP 61-123635; however, see English language equivalent U.S. Pat. No. 4,631,208. Original Document extracted from the espacenet.com database on Jul. 26, 2012, 7 pages.
English language abstract not available for WO 93/10748; however, see English language equivalent U.S. Pat. No. 5,609,167. Original document extracted from espacenet.com database on Aug. 28, 2012, 22 pages.
International Preliminary Report on Patentability, PCT/JP2010/069248 (dated May 15, 2012), 7 pages.
International Search Report for Application No. PCT/JP2010/069237 dated Jan. 11, 2011, 6 pages.
International Search Report for Application No. PCT/JP2010/069248 dated Jan. 11, 2011, 4 pages.
International Search Report for Application No. PCT/JP2010/069249 dated Jan. 11, 2011, 6 pages.
International Search Report for Application No. PCT/JP2010/073668 dated Jun. 22, 2014, 4 pages.
International Search Report for PCT/JP2012/084279 dated Oct. 11, 2013, 6 pages.
MPEP Chapter 1800, Section 1850, Rev. 7, Jul. 2008, pp. 85-91 (7 pages).
Murthy, Ranjini et al., "Protein-Resistant Silicones: Incorporation of Poly(ethylene oxide) via Siloxane Tethers", Biomacromolecules Aug. 2007, pp. 3244-3252.
Shin-Etsu, Shin-Etsu Silicone, Silicone Products for Personal Care, [Retrieved from internet <URL: http://www.shinetsusilicones.com/files/literature/Shin-Etsu%20Unique%20Ma-terials%202010%2011.sub.-2.pdf >], dated Nov. 2010, 20 pages.
Supplementary European Search Report for Application No. EP 10 82 5093 dated May 16, 2013; 2 pages.
Supplementary European Search Report for Application No. EP 10 82 5094 completed on Dec. 11, 2013, 2 pages.
Machine-assisted English translation for JPS 55-41210 extracted from espacenet.com database on Nov. 4, 2017, 3 pages.
Machine-assisted English translation for JPS 50-004199 extracted from espacenet.com database on Nov. 4, 2017, 6 pages.
Machine-assisted English translation for JPS 57-139123 extracted from espacenet.com database on Nov. 4, 2017, 9 pages.
English language abstract and machine-assisted English translation for JP 2005-330221extracted from espacenet.com database on Oct. 16, 2017, 17 pages.
English language abstract and machine-assisted English translation for JP 2005-344076 extracted from espacenet.com database on Oct. 16, 2017, 21 pages.
English language abstract for WO 2012/165228 extracted from espacenet.com database on Oct. 16, 2017, 2 pages.
English language abstract for WO 2012/165237 extracted from espacenet.com database on Oct. 16, 2017, 2 pages.
English language abstract and machine-assisted English translation for JP 09-194594 extracted from the PAJ database on Nov. 26, 2012, 56 pages.
English language abstract and machine-assisted English translation for JP 10-167946 extracted from the PAJ database on Nov. 26, 2012, 27 pages.
English language abstract and machine-assisted English translation for JP 2000-128740 extracted from PAJ database on Aug. 28, 2012, 29 pages.
English language abstract and machine-assisted English translation for JP 2000-143458 extracted from espacenet.com database on Aug. 28, 2012, 29 pages.
English language abstract and machine-assisted English translation for JP 6089147 extracted from the espacenet.com and PAJ databases on Nov. 26, 2012, 54 pages.
English language abstract and machine-assisted English translation for JP2005089494 extracted from espacenet.com database on Sep. 9, 2014, 18 pages.
English language abstract and machine-assisted English translation for JP2005120293 extracted from espacenet.com database on Sep. 9, 2014, 48 pages.
English language abstract and machine-assisted English translation for JP2844453 extracted from espacenet.com database on Sep. 9, 2014, 16 pages.
English language abstract and machine-assisted English translation for JPH07330907 extracted from espacenet.com database on Sep. 9, 2014, 10 pages.
English language abstract and machine-assisted English translation for JPH09165315 extracted from espacenet.com database on Sep. 9, 2014, 12 pages.
English language abstract and machine-assisted English translation for JPH09165318 extracted from espacenet.com database on Sep. 9, 2014, 12 pages.
English language abstract and machine-assisted English translation for WO 2008/004502 extracted from espacenet.com database on Aug. 28, 2012, 92 pages.
English language abstract and machine-assisted English translation for WO 2005/054341 extracted from espacenet.com database on Aug. 28, 2012, 168 pages.
English language abstract and machine-assisted English translation for WO 94/16677 extracted from espacenet.com database on Aug. 28, 2012, 29 pages.
English language abstract and machine-assisted translation for JP 05-112424 extracted from the PAJ database on Jul. 16, 2012, 80 pages.
English language abstract and machine-assisted translation for JP 05-163436 extracted from the PAJ database on Jul. 26, 2012, 26 pages.
English language abstract and machine-assisted translation for JP 05-186596 extracted from the PAJ database on Jul. 12, 2012, 52 pages.
English language abstract and machine-assisted translation for JP 06-157236 extracted from the PAJ database on Jul. 13, 2012, 26 pages.
English language abstract and machine-assisted translation for JP 06-305933 extracted from the PAJ database on Jul. 16, 2012, 36 pages.
English language abstract and machine-assisted translation for JP 07-025728 extracted from the PAJ database on Jul. 16, 2012, 39 pages.
English language abstract and machine-assisted translation for JP 07-033622 extracted from the PAJ database on Jul. 16, 2012, 40 pages.
English language abstract and machine-assisted translation for JP 07-100358 extracted from the PAJ database on Jul. 26, 2012, 29 pages.
English language abstract and machine-assisted translation for JP 07-187945 extracted from the PAJ database on Jul. 13, 2012, 56 pages.
English language abstract and machine-assisted translation for JP 08-217626 extracted from the PAJ database on Jul. 26, 2012, 53 pages.
English language abstract and machine-assisted translation for JP 08-268831 extracted from the PAJ database on Jul. 26, 2012, 35 pages.
English language abstract and machine-assisted translation for JP 08-268832 extracted from the PAJ database on Jul. 26, 2012, 47 pages.
English language abstract and machine-assisted translation for JP 09-071504 extracted from the PAJ database on Jul. 13, 2012, 29 pages.
English language abstract and machine-assisted translation for JP 09-194323 extracted from the PAJ database on Jul. 26, 2012, 31 pages.

(56) References Cited

OTHER PUBLICATIONS

English language abstract and machine-assisted translation for JP 10-245317 extracted from the PAJ database on Jul. 26, 2012, 39 pages.
English language abstract and machine-assisted translation for JP 10-310504 extracted from the PAJ database on Jul. 13, 2012, 33 pages.
English language abstract and machine-assisted translation for JP 10-310505 extracted from the PAJ database on Jul. 13, 2012, 28 pages.
English language abstract and machine-assisted translation for JP 10-310506 extracted from the PAJ database on Jul. 13, 2012, 29 pages.
English language abstract and machine-assisted translation for JP 10-310507 extracted from the PAJ database on Jul. 13, 2012, 30 pages.
English language abstract and machine-assisted translation for JP 10-310508 extracted from the PAJ database on Jul. 13, 2012, 33 pages.
English language abstract and machine-assisted translation for JP 10-310509 extracted from the PAJ database on Jul. 13, 2012, 33 pages.
English language abstract and machine-assisted translation for JP 10-316536 extracted from the PAJ database on Jul. 16, 2012, 29 pages.
English language abstract and machine-assisted translation for JP 2000-063225 extracted from the PAJ database on Jul. 16, 2012, 61 pages.
English language abstract and machine-assisted translation for JP 2001-316473 extracted from the PAJ database on Jul. 26, 2012, 45 pages.
English language abstract and machine-assisted translation for JP 2002-179797 extracted from PAJ database on Jul. 13, 2012, 67 pages.
English language abstract and machine-assisted translation for JP 2004-182680 extracted from the PAJ database on Jul. 26, 2012, 96 pages.
English language abstract and machine-assisted translation for JP 2004-231608 extracted from the PAJ database on Jul. 26, 2012, 75 pages.
English language abstract and machine-assisted translation for JP 2005-194523 extracted from the PAJ database on Jul. 26, 2012, 53 pages.
English language abstract for JP 02-583412 extracted from the espacenet.com and machine-assisted translation extracted from the PAJ database on Jul. 12, 2012, 22 pages.
English language abstract for JP 02-719303 extracted from the espacenet.com database and machine-assisted translation extracted from the PAJ database on Jul. 16, 2012, 24 pages.
English language abstract for JP 04-211605 extracted from the espacenet.com database on Jul. 26, 2012, 8 pages.
English language abstract for JP 04-234307 extracted from the espacenet.com database on Jul. 26, 2012, 9 pages.
English language abstract for JP 05-311076 extracted from the espacenet.com database on Jul. 26, 2012, 14 pages.
English language abstract for JP 11-049957 extracted from the espacenet.com database on Jul. 16, 2012, 9 pages.
English language abstract for JP 2000-072784 extracted from the espacenet.com database on Jul. 17, 2012, 13 pages.
English language abstract for JP 2000-239390 extracted from the espacenet.com database on Jul. 17, 2012, 14 pages.

\* cited by examiner

METHOD FOR PRODUCING TRANSPARENT OR SEMI-TRANSPARENT LIQUID GLYCERIN-DERIVATIVE-MODIFIED SILICONE COMPOSITION

RELATED APPLICATIONS

This application is the National Stage of International Patent Application No. PCT/JP2013/085007, filed on Dec. 26, 2013, which claims priority to and all the advantages of Japanese Patent Application No. 2012-288071, filed on Dec. 28, 2012, the content of which is incorporated herein by reference.

TECHNICAL FIELD

The present invention relates to a method for producing a transparent or semi-transparent (translucent) liquid glycerin derivative-modified silicone composition. Furthermore, the present invention relates to the use of the glycerin derivative-modified silicone in external use preparations, cosmetics, and various industrial materials.

BACKGROUND ART

As silicones having a hydrophilic group, a variety of modified silicone compounds are known, and among non-ionic systems, polyether-modified silicones have been widely used since the past. Additionally, (poly)glycerin-modified silicones (Patent Documents 1 to 9) and sugar- and polysaccharide-modified silicone compounds (Patent Document 10) have also been reported. Low-HLB polyether-modified silicones are outstanding emulsifiers capable of providing W/O emulsions with excellent stability while having fluidity with low viscosity, and therefore have been widely used particularly in the field of cosmetic products.

In contrast, silicones modified with polyglycerins, sugars, or polysaccharides have the problems that the degree of freedom in structural design is low and they do not have a wide range of use. These polyhydric alcohol-modified silicones are normally produced by adding a polyhydric alcohol derivative containing a reactive unsaturated group to an organohydrogensiloxane, but in many cases, miscibility of residual polyhydric alcohol derivative and the polyhydric alcohol-modified silicone that is the reaction product is low, and the appearance is cloudy and non-uniform, and phase separation occurs within a short time after production.

Additionally, because miscibility of organohydrogenpolysiloxanes and polyhydric alcohol derivatives is inherently low, if the molecular weight of a polyhydric alcohol-modified silicone exceeds roughly 5000, there has been the problem that the addition reaction does not come to completion even if a solvent is used, and production of the targeted product is often difficult. Furthermore, even when the molecular weight is approximately 3000, there has been a problem from the viewpoint of production efficiency as well, in that unreacted matter gradually separates and settles and an operation to remove it is required.

Furthermore, even if a compound in which the hydroxyl group is protected is used as the polyhydric alcohol derivative, the problem of separation described above is unavoidable because deprotection is necessary after the reaction ends. Also, with this method, acid treatment conditions for deprotection are inevitably harsh and breakage of the silicone backbone occurs, and as a result, there is the problem that the desired product cannot be obtained with good reproducibility.

Patent Document 7 proposes a method for producing a branched polyglycerol-modified silicone obtained by adding/graft polymerizing a silicone having at least one functional group selected from the group consisting of hydroxy groups, carboxy groups, amino groups, imino groups, mercapto groups, and epoxy groups, with 2,3-epoxy-1-propanol in the presence of an acidic or basic catalyst. With this method, however, the siloxane backbone breaks during graft polymerization, and as a result, two or more components having different properties tend to be produced as copolymers, and there are many problems from the perspectives of quality and the purification process.

In response to these problems, it has been attempted to improve transparency of polyhydric alcohol-modified silicone compositions that are reaction products by reducing the amount of residual polyhydric alcohol derivative, which causes cloudiness and phase separation, by repeating microfiltration and adsorbent treatment. However, these impurities are ordinarily liquids in the temperature range in which the polyhydric alcohol-modified silicone that is the main component is in the liquid phase, and therefore a technique of solid/liquid separation utilizing a filter aid, a cartridge filter, or the like is not only irrational, but is also mostly ineffective in actuality. For this reason, after the majority of the impurities are first extracted out in a highly hydrophilic solvent, an operation of further removing residual liquid impurities from the polyhydric alcohol-modified silicone that is the main component by a filtration process using an adsorbent such as activated carbon is required (or, conversely, the main component is extracted in a hydrophilic solvent). Incidentally, phase separation in the extraction process ordinarily takes time, and this does not yield clean separation. This results in an increase in waste and a decrease in yield and productivity. Furthermore, in many cases the system as a whole goes into an emulsified state and separation is impossible due to the structure of polyhydric alcohol-modified silicone, and since it cannot be generally used from the perspective of industrial production, this problem is still not resolved at present.

Recently, Patent Document 8 has proposed a novel alternating copolymer of organopolysiloxane with polyglycerine derivative, and suggests that a high molecular weight polyglycerine-modified silicone can be obtained without the problem of white turbidness, and the like, caused by the unreacted starting material occurring. However, it is clear from the chemical structure that this compound has a hydrophilic group portion incorporated on its backbone. As a result, this copolymer has properties completely different that those of conventional general-use hydrophilic silicones such as polyether-modified silicone and the like and, therefore, a high level of technical skill is necessary to stably compound this copolymer in delicate formulations such as cosmetic products and the like, leading to the problem of the field of use being limited.

For the reasons described above, the current situation is that conventional polyhydric alcohol-modified silicones have little practical utility and inevitably lack variation in chemical structure. Therefore, there has been a demand for the development of a stable polyhydric alcohol-modified silicone that is easy to produce and incurs almost no phase separation or sedimentation of unreacted starting material or the like after production, and a method for producing the same.

Thus, in Patent Document 11, the present inventors disclose a novel organopolysiloxane containing a hydrophilic group, which is easy to produce and incurs almost no phase separation or sedimentation of unreacted starting material and the like after production, and is chemically stable and has excellent practicality, and a method for producing the same. In particular, they propose that this organopolysiloxane be used as a surfactant, powder treatment agent, and surface treatment agent that can be advantageously used in the field of cosmetics.

The novel organopolysiloxanes containing a hydrophilic group produced by the technique disclosed in Patent Document 11 are uniform and stable compositions, but since many of them appear cloudy or translucent, they sometimes have the problem that they simply look unattractive, depending on the user. Additionally, from the presumption that an opaque appearance implies low miscibility between the main component and impurities, there have been also users who have concerns about the possibility of potential phase separation after the quality guarantee period of the product elapsed even if there is no problem within that period. In these respects, there has been still room for improvement in the novel organopolysiloxanes containing a hydrophilic group proposed in the past by the present applicants (Patent Document 11).

PRIOR ART DOCUMENT

Patent Document

Patent Document 1: Japanese Examined Patent Application Publication No. S62-34039A
Patent Document 2: Japanese Unexamined Patent Application Publication No. S62-195389A (Japanese Patent No. 2583412B)
Patent Document 3: Japanese Examined Patent Application Publication No. H06-089147 (Japanese Patent No. 1956013B)
Patent Document 4: Japanese Patent No. 2613124B (Japanese Unexamined Patent Application Publication No. H04-188795A)
Patent Document 5: Japanese Patent No. 2844453B (Japanese Unexamined Patent Application Publication No. H02-228958A)
Patent Document 6: Japanese Patent No. 3976226B (Japanese Unexamined Patent Application Publication No. 2002-179798A)
Patent Document 7: Japanese Patent No. 4485134B (Japanese Unexamined Patent Application Publication No. 2004-339244A)
Patent Document 8: Japanese Patent No. 5037782B (Japanese Unexamined Patent Application Publication No. 2005-042097A)
Patent Document 9: Japanese Patent No. 4357909B (Japanese Unexamined Patent Application Publication No. 2005-089494A)
Patent Document 10: Japanese Unexamined Patent Application Publication No. H05-186596A
Patent Document 11: WO/2011/049248
Patent Document 12: WO/2011/049247
Patent Document 13: WO/2011/049246
Patent Document 14: Japanese Unexamined Patent Application Publication No. 2012-046507A

SUMMARY OF INVENTION

Technical Problem

An object of the present invention is to provide a liquid glycerin derivative-modified silicone composition having a transparent or semi-transparent appearance. In particular, an object of the present invention is to provide a liquid glycerin derivative-modified silicone composition having high transparency and having transparency that is stable regardless of temperature environment.

Another object of the present invention is to provide a liquid glycerin derivative-modified silicone composition having a stable transparent or semi-transparent appearance, containing a glycerin derivative-modified silicone having chemical stability and excellent practicality, that is easy to produce, has excellent yield and productivity with little waste, and incurs absolutely no phase separation or sedimentation of unreacted starting materials or the like after production.

A further object of the present invention is to use the transparent or semi-transparent liquid glycerin derivative-modified silicone produced by such a method in external use preparations, cosmetics, or various industrial materials.

Solution to Problem

The objects of the present invention are achieved by a method for producing a transparent or semi-transparent liquid glycerin derivative-modified silicone composition that includes a hydration step of adding water to a liquid glycerin derivative-modified silicone or composition thereof.

In the hydration step, from 0.1 to 10 parts by mass of water per 100 parts by mass of the liquid glycerin derivative-modified silicone or composition thereof may be added.

In the hydration step, the liquid glycerin derivative-modified silicone or composition thereof and the water are preferably mixed to homogenize.

The visible light transmittance of the transparent or semi-transparent liquid glycerin derivative-modified silicone composition is preferably not less than 70%, and the light transmittance at 750 nm (optical path length 10 mm) is particularly preferably not less than 50%.

The glycerin derivative-modified silicone can be represented by the following general formula (1):
[Formula 1]

(wherein $R^1$ represents a monovalent organic group (however, excluding $R^2$, L, and Q), a hydrogen atom or a hydroxyl group; and $R^2$ is a substituted or unsubstituted, straight or branched monovalent hydrocarbon group having 9 to 60 carbon atoms, or the chain organosiloxane group represented by the following general formula (2-1):

[Formula 2]

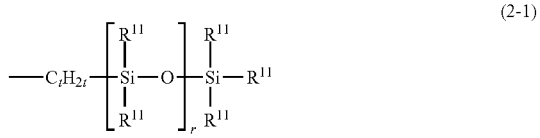

(wherein $R^{11}$ are each independently a substituted or unsubstituted monovalent hydrocarbon group having from 1 to 30 carbon atoms, hydroxyl groups, or hydrogen atoms and at least one of the $R^{11}$ moieties is the monovalent hydrocarbon group; t is a number in a range of 2 to 10; and r is a number in a range of 1 to 500); or the general formula (2-2) below:

[Formula 3]

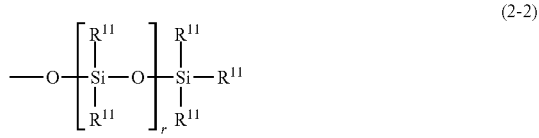

(2-2)

(wherein, $R^{11}$ and r are synonymous with those described above); and $L^1$ represents a silylalkyl group having a siloxane dendron structure represented by the following general formula (3) when i=1;

[Formula 4]

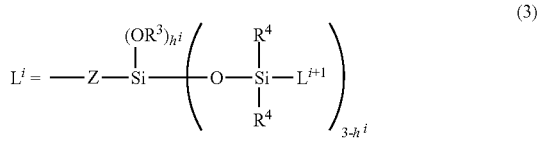

(3)

(wherein $R^3$ each independently represent a substituted or unsubstituted, straight or branched monovalent hydrocarbon group having from 1 to 30 carbon atoms; $R^4$ each independently represent an alkyl group or phenyl group having from 1 to 6 carbon atoms; Z represents a divalent organic group; i represents a generation of the silylalkyl group represented by $L^i$ and is an integer from 1 to k when k is a number of generations that is a number of repetitions of the silylalkyl group; the number of generations k is an integer from 1 to 10; $L^{i+1}$ is the silylalkyl group when i is less than k, and $R^4$ when i=k, and $h^i$ is a number in a range of 0 to 3); Q represents a glycerin derivative group; and a, b, c, and d are each numbers in the ranges of $1.0 \le a \le 2.5$, $0 \le b \le 1.5$, $0 \le c \le 1.5$, and $0.0001 \le d \le 1.5$.

The production method of the present invention may further comprise, before and/or after and/or simultaneously with the hydration step, a liquid oil agent addition step of adding a liquid oil agent to the liquid glycerin derivative-modified silicone or composition thereof.

The liquid oil agent and the liquid glycerin derivative-modified silicone preferably have affinity.

In the liquid oil addition step, from 5 to 1000 parts by mass of liquid oil agent per 100 parts by mass of the liquid glycerin derivative-modified silicone or composition thereof may be added.

In the liquid oil agent addition step, the liquid glycerin derivative-modified silicone or composition thereof and the liquid oil agent are preferably mixed to homogenize.

In the present invention, the glycerin derivative-modified silicone or composition thereof is preferably treated with an acidic aqueous solution, and water and odor-causing substances produced by treatment with the acidic aqueous solution are preferably removed by heating or depressurization.

The present invention also relates to a transparent or semi-transparent liquid glycerin derivative-modified silicone composition obtained by the production method of the present invention.

The objects of the present invention are also achieved by an external use preparation, a cosmetic, or an industrial material containing a transparent or semi-transparent liquid glycerin derivative-modified silicone composition obtained by the production method of the present invention.

Advantageous Effects of Invention

The production method of the present invention can provide a liquid glycerin derivative-modified silicone composition having a transparent or semi-transparent appearance. In particular, the liquid glycerin derivative-modified silicone composition obtained by the present invention has high transparency and has transparency that is stable regardless of temperature environment.

Additionally, the present invention can provide a liquid glycerin derivative-modified silicone composition having a stable transparent or semi-transparent appearance, containing a glycerin derivative-modified silicone having chemical stability and excellent practicality that is easy to produce, has excellent yield and productivity with little waste, and incurs absolutely no phase separation or sedimentation of unreacted starting materials or the like after production.

In addition, a transparent or semi-transparent glycerin derivative-modified silicone obtained by the production method of the present invention can be preferably used in external use preparations or cosmetics and can further be widely used in various industrial materials.

In particular, because the liquid glycerin derivative-modified silicone composition obtained by the present invention has stable viscosity regardless of temperature environment, it is superior in ease of handling, and can stabilize the viscosity of an external use preparation or cosmetic in which it is blended.

DESCRIPTION OF EMBODIMENTS

A first aspect of the present invention is a method for producing a transparent or semi-transparent liquid glycerin derivative-modified silicone composition that includes a hydration step of adding water to a liquid glycerin derivative-modified silicone or composition thereof.

The first aspect of the present invention will be described in detail hereinafter.

[Glycerin Derivative-Modified Silicone]

The glycerin derivative-modified silicone to which the present invention can be applied is a silicone compound modified with a glycerin derivative and is a liquid composition, and it is preferably a liquid at least at a temperature of 100° C. The chemical structure or the like is not particularly limited as long as the composition satisfies this condition.

In the present invention, a "liquid form" or a "liquid" means that after the liquid surface of an organopolysiloxane in a prescribed container is placed horizontally and the vessel is then inclined, the liquid surface can once again become horizontal after 1 hour, preferably after 30 minutes, and more preferably after 10 minutes. Here, "horizontal" means to form a plane that intersects the direction of gravitational force at a right angle. The glycerin derivative-modified silicone is preferably a liquid at least at 100° C. but more preferably also exhibits liquidity in a range of 100° C. or less to room temperature. Specifically, the glycerin derivative-modified silicone is preferably a liquid at 80° C., more preferably a liquid at 40° C., and even more preferably a liquid at room temperature (25° C.). Compositions that are in the liquid state at a temperature of not less than 100° C. are, of course, included in the scope of the liquid glycerin derivative-modified silicone, but glycerin derivative-modified silicones that demonstrate liquidity when heated to, for example, 100° C. even if they are in a semi-gelatinous form or a soft solid form without fluidity at room temperature (25° C.) or lower are also included.

The glycerin derivative-modified silicone can be represented by the following general formula (1):
[Formula 5]

(wherein $R^1$ represents a monovalent organic group (however, excluding $R^2$, L, and Q), a hydrogen atom or a hydroxyl group; and $R^2$ is a substituted or unsubstituted, straight or branched monovalent hydrocarbon group having from 9 to 60 carbon atoms, or the chain organosiloxane group represented by the following general formula (2-1):

[Formula 6]

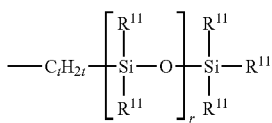

(wherein $R^{11}$ are each independently a substituted or unsubstituted monovalent hydrocarbon group having from 1 to 30 carbon atoms, hydroxyl groups, or hydrogen atoms and at least one of the $R^{11}$ moieties is the monovalent hydrocarbon group; t is a number in a range of 2 to 10; and r is a number in a range of 1 to 500); or the general formula (2-2) below:

[Formula 7]

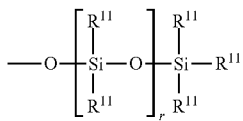

(wherein, $R^{11}$ and r are synonymous with those described above); and $L^1$ represents a silylalkyl group having a siloxane dendron structure represented by the following general formula (3) when i=1;

[Formula 8]

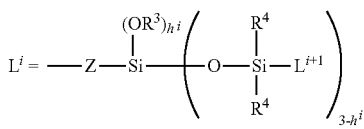

(wherein $R^3$ each independently represent a substituted or unsubstituted, straight or branched monovalent hydrocarbon group having from 1 to 30 carbon atoms; $R^4$ each independently represent an alkyl group or phenyl group having from 1 to 6 carbon atoms; Z represents a divalent organic group; i represents a generation of the silylalkyl group represented by $L^i$ and is an integer from 1 to k when k is a number of generations that is a number of repetitions of the silylalkyl group; the number of generations k is an integer from 1 to 10; $L^{i+1}$ is the silylalkyl group when i is less than k, and $R^4$ when i=k, and $h^i$ is a number in a range of 0 to 3); Q represents a glycerin derivative group; and a, b, c, and d are each numbers in the ranges of $1.0 \le a \le 2.5$, $0 \le b \le 1.5$, $0 \le c \le 1.5$, and $0.0001 \le d \le 1.5$.

Here, when the glycerin derivative-modified silicone represented by general formula (1) has the long chain organic group or the chain organosiloxane group represented by $R^2$, b is a number greater than 0, preferably $0.0001 \le b \le 1.5$, and more preferably $0.001 \le b \le 1.5$. Similarly, when the glycerin derivative-modified silicone represented by general formula (1) has a silylalkyl group having the siloxane dendron structure represented by $L^1$, c is a number greater than 0, preferably $0.0001 \le c \le 1.5$, and more preferably $0.001 \le c \le 1.5$.

The glycerin derivative-modified silicone preferably has a long chain organic group or chain organosiloxane group represented by $R^2$ or a siloxane dendron structure represented by $L^1$ together with the glycerin derivative group serving as Q.

At this time, the suitable values of b and c are represented as follows by essential functional groups.
(1) When there is a group represented by $R^2$: $0.001 \le b \le 1.5$ and $0 \le c \le 1.5$.
(2) When there is a group represented by $L^1$: $0 \le b \le 1.5$ and $0.001 \le c \le 1.5$.
(3) When there are both a group represented by $R^2$ and a group represented by $L^1$: $0.001 \le b \le 1.5$ and $0.001 \le c \le 1.5$.

The monovalent groups represented by $R^1$ in general formula can be the same or different and are not particularly limited as long as they are not the functional groups of $R^2$, $L^1$, and Q. However, they are preferably a substituted or unsubstituted, straight-chain or branched monovalent hydrocarbon group having from 1 to 8 carbon atoms, a (poly) oxyalkylene group represented by $—R^5O(AO)_nR^6$ (in the formula, AO represents an oxyalkylene group having from 2 to 4 carbon atoms; $R^5$ represents a substituted or unsubstituted, straight-chain or branched divalent hydrocarbon group having from 3 to 5 carbon atoms; $R^6$ represents a substituted or unsubstituted, straight-chain or branched monovalent hydrocarbon group having from 1 to 24 carbon atoms and hydrogen atoms or a substituted or unsubstituted, straight-chain or branched acyl group having from 2 to 24 carbon atoms; and n is from 1 to 100), an alkoxy group, a hydroxyl group, or a hydrogen atom. However, not all of the $R^1$ moieties are hydroxyl groups, hydrogen atoms, alkoxy groups, or (poly)oxyalkylene groups.

Examples of a monovalent hydrocarbon group having 1 to 8 carbon atoms are, for example, alkyl groups such as a methyl group, ethyl group, propyl group, butyl group, pentyl group, hexyl group, heptyl group, octyl group, and the like; cycloalkyl groups such as a cyclopentyl group, cyclohexyl group, and the like; alkenyl groups such as a vinyl group, allyl group, butenyl group, and the like; aryl groups such as a phenyl group, tolyl group, and the like; aralkyl groups such as a benzyl group; and groups wherein the hydrogen atoms bonded to the carbon atoms of these groups are substituted at least partially by fluorine or a similar halogen atom, or an organic group having an epoxy group, a glycidyl group, an acyl group, a carboxyl group, an amino group, a (meth)acryl group, a mercapto group, or the like (however, the total number of carbon atoms is from 1 to 8). The monovalent hydrocarbon group is preferably a group other than an alkenyl group, and is particularly preferably a methyl group, an ethyl group, or a phenyl group. Additionally, examples of the alkoxy group include a methoxy group, an ethoxy group, an isopropoxy group, a butoxy group, and similar lower alkoxy groups; a lauryl alkoxy group, a myristyl alkoxy group, a palmityl alkoxy group, an oleyl alkoxy group, a stearyl alkoxy group, a behenyl alkoxy group, and similar higher alkoxy groups; and the like.

Particularly, the $R^1$ moieties are preferably monovalent hydrocarbon groups having from 1 to 8 carbon atoms and that are free of unsaturated aliphatic bonds or monovalent fluorinated hydrocarbon groups. Examples of the monovalent hydrocarbon group not having unsaturated aliphatic bonds belonging to the $R^1$ moiety include methyl groups, ethyl groups, propyl groups, butyl groups, pentyl groups, hexyl groups, and similar alkyl groups; phenyl groups, tolyl groups, xylyl groups, and similar aryl groups; and aralkyl groups such as benzyl groups. Examples of the monovalent fluorinated hydrocarbon group include trifluoropropyl groups, pentafluoroethyl groups, and similar perfluoroalkyl groups. From an industrial perspective, $R^1$ is preferably a methyl group, an ethyl group, or a phenyl group, and more preferably from 90 mol % to 100 mol % of all the $R^1$ moieties are selected from methyl groups, ethyl groups, or phenyl groups.

A glycerin derivative-modified silicone aims at imparting additional functionality, and it is possible to introduce or design a modified group other than a hydrophilic group (-Q), particularly a short chain or medium chain hydrocarbon based group, as $R^1$. Specifically, when $R^1$ is a substituted monovalent hydrocarbon group, a substituent can be preferably selected in accordance with desired characteristics and uses. For example, when using the glycerin derivative-modified silicone as a cosmetic composition or a fiber treating agent raw material, it is possible to introduce an amino group, amide group, aminoethyl aminopropyl group, carboxyl group, and the like, as the substituted group of a monovalent hydrocarbon group, for the purpose of improving the sensation during use, feeling to touch, persistence, and the like.

The substituted or unsubstituted, straight or branched monovalent hydrocarbon group having from 9 to 60 carbon atoms of $R^2$ of general formula (1) is a long chain hydrocarbon group or a chain organosiloxane group represented by general formula (2-1) or (2-2). By introducing this group at the main chain and/or side chain of polysiloxane, it is possible to further improve the affinity, emulsifiability, and dispersibility, and further the sensation during use of various components such as an oil agent, powder, or the like incorporated in an external use preparation or a cosmetic composition. Furthermore, because the monovalent long chain hydrocarbon group or chain organopolysiloxane group is a hydrophobic functional group, the compounding stability and the compatibility with organic oils having a high content of alkyl groups are further improved. $R^2$ may be all the monovalent long chain hydrocarbon group or all the chain organopolysiloxane group, or may be a functional group of both of these groups. In the glycerin derivative-modified silicone, it is particularly preferable that part or all of $R^2$ is a monovalent long chain hydrocarbon group, and by having such a monovalent long chain hydrocarbon group in a molecule, the glycerin derivative-modified silicone exhibits more superior compatibility not only with silicone oil, but with non silicone oil with a high alkyl group content as well. For example, it is possible to obtain an emulsion and a dispersion with superior stability over time and thermal stability, which are made of non silicone oil.

Substituted or unsubstituted, straight or branched monovalent hydrocarbon groups that are represented by $R^2$ of general formula (1), that are bonded to silicon atoms, and that have from 9 to 60 carbon atoms, may be the same or different. Furthermore, the structure thereof is selected from among straight chain, branched, and partially branched. In the present invention, it is particularly preferable for R2 to be an unsubstituted straight chain monovalent hydrocarbon group. An unsubstituted monovalent hydrocarbon group can be, for example, an alkyl group, aryl group, or aralkyl group having from 9 to 60 carbon atoms, preferably from 9 to 30 carbon atoms, and more preferably from 10 to 25 carbon atoms. On the other hand, examples of the substituted monovalent hydrocarbon group include perfluoroalkyl groups, aminoalkyl groups, amide alkyl groups, and ester groups having from 9 to 30 carbon atoms, preferably from 9 to 30 carbon atoms, and more preferably from 10 to 24 carbon atoms. Additionally, the carbon atoms of the monovalent hydrocarbon groups may be partially substituted with alkoxy groups, and examples of said alkoxy groups include methoxy groups, ethoxy groups, and propoxy groups. This type of monovalent hydrocarbon group is particularly preferably an alkyl group having from 9 to 30 carbon atoms, and an example thereof is a group represented by the general formula $-(CH_2)_v-CH_3$ (v is a number in a range of 8 to 29). Particularly, an alkyl group having from 10 to 24 carbon atoms is preferable.

The chain organosiloxane group in general formula (2-1) or (2-2) has a straight chain polysiloxane chain structure, unlike a silylalkyl group, which has a siloxane dendron structure. In general formula (2-1) or (2-2), $R^{11}$ are each independently a substituted or unsubstituted monovalent hydrocarbon group having from 1 to 30 carbon atoms, a hydroxyl group, or a hydrogen atom. The substituted or unsubstituted monovalent hydrocarbon group having from 1 to 30 carbon atoms is preferably an alkyl group having from 1 to 30 carbon atoms, an aryl group having from 6 to 30 carbon atoms, an aralkyl group having from 6 to 30 carbon atoms, or a cycloalkyl group having from 6 to 30 carbon atoms, and is exemplified by a methyl group, ethyl group, propyl group, butyl group, pentyl group, hexyl group, heptyl group, octyl group, decyl group, or other alkyl group; a cyclopentyl group, cyclohexyl group, or other cycloalkyl group; or a phenyl group, tolyl group, or other aryl group. The hydrogen atoms bonded to the carbon atoms of these groups may be substituted at least partially by fluorine or a similar halogen atom, or an organic group containing an epoxy group, acyl group, carboxyl group, amino group, methacryl group, mercapto group, or the like. A methyl group, a phenyl group, or a hydroxyl group is particularly preferable as $R^{11}$. A configuration in which a part of $R^{11}$ is a methyl group and another part of $R^{11}$ is a long chain alkyl group having from 8 to 30 carbon atoms is also preferable.

In general formula (2-1) or (2-2), t is a number in a range of 2 to 10; r is a number in a range of 1 to 500; and r preferably is a number in a range of 2 to 500. Such a straight chain organosiloxane group is hydrophobic. From the standpoint of compatibility with various oil agents, r preferably is a number in a range of 1 to 100, and particularly preferably is a number in a range of 2 to 30.

A silylalkyl group having a siloxane dendron structure shown by general formula (3) is a functional group that includes a structure wherein a carbosiloxane unit spreads in a dendrimer shape and that exhibits high water repellence. The silylalkyl group is well-balanced when combined with hydrophilic groups, and when an external use preparation or cosmetic composition that incorporates the glycerin derivative-modified silicone is used, the silylalkyl group inhibits an unpleasant sticky feeling, and provides a refreshingly natural feeling to the touch. Additionally, the silylalkyl group having a siloxane dendron structure is chemically stable, and for this reason, the silylalkyl group is a functional group providing advantageous properties such as usability in combination with a wide range of components.

Examples of the substituted or unsubstituted, straight or branched monovalent hydrocarbon group having from 1 to 30 carbon atoms (the $R^3$ moieties in general formula (3)) include methyl groups, ethyl groups, propyl groups, butyl groups, pentyl groups, hexyl groups, heptyl groups, octyl groups, and similar alkyl groups; cyclopentyl groups, cyclohexyl groups, and similar cycloalkyl groups; vinyl groups, allyl groups, butenyl groups, and similar alkenyl groups; phenyl groups, tolyl groups, and similar aryl groups; benzyl groups and similar aralkyl groups; and groups wherein the hydrogen atoms bonded to the carbon atoms of these groups are substituted at least partially by fluorine or a similar halogen atom, or an organic group containing an epoxy group, a glycidyl group, an acyl group, a carboxyl group, an amino group, a methacryl group, a mercapto group, or the like (provided that the total number of carbon atoms is from 1 to 30).

Among the phenyl group or the alkyl group having from 1 to 6 carbon atoms represented by $R^4$ in general formula (3), examples of the alkyl group having from 1 to 6 carbon atoms include methyl, ethyl, n-propyl, i-propyl, n-butyl, i-butyl, s-butyl, pentyl, neopentyl, cyclopentyl, hexyl, and similar straight, branched, or cyclic alkyl groups.

In the general formula (3), in the case of i=k, $R^4$ is preferably a methyl group or a phenyl group. In particular, R4 is preferably a methyl group when i=k.

From an industrial standpoint, the number of generations k is preferably an integer from 1 to 3, and more preferably is 1 or 2. In each of the number of generations, the group represented by $L^1$ is represented as follows. In the formulae, $R^3$, $R^4$, and Z are the same groups as described above.

When the number of generations is k=1, $L^1$ is represented by the following general formula (3-1).

[Formula 9]

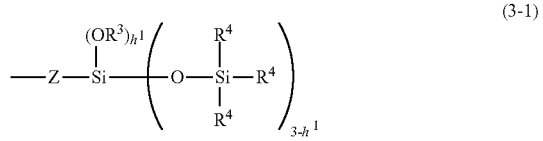

(3-1)

When the number of generations is k=2, $L^1$ is represented by the following general formula (3-2).

[Formula 10]

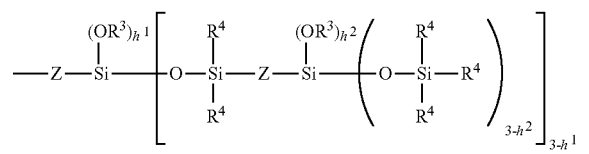

(3-2)

When the number of generations is k=3, $L^1$ is represented by the following general formula (3-3).

[Formula 11]

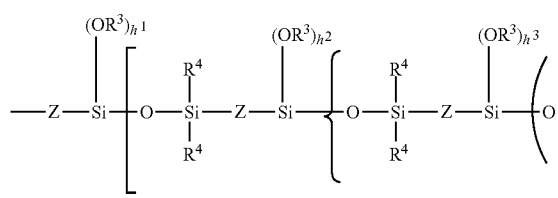

(3-3)

In the structures represented by the general formulae (3-1) to (3-3) in the case of the number of generations is from 1 to 3, each of $h^1$, $h^2$ and $h^3$ moieties is independently a number in a range of 0 to 3. These $h^i$ moieties are preferably a number in a range of 0 to 1, and $h^i$ is, in particular, preferably 0.

In general formulae (3) and (3-1) to (3-3), Z are each independently a divalent organic group, and specific examples thereof include a divalent organic group formed by addition-reacting a silicon-bonded hydrogen atom and a functional group having an unsaturated hydrocarbon group such as an alkenyl group, an acryloxy group, a methacryloxy group, or the like at the terminal. Depending on the method for introducing the silylalkyl group having a siloxane dendron structure, the functional group can be appropriately selected and is not restricted to the functional groups described above. Preferably, Z are each independently a group selected from divalent organic groups represented by the following general formula.

[Formula 12]

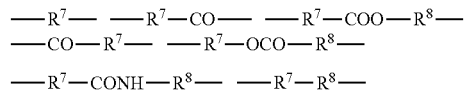

Of these, Z in $L^1$ is preferably a divalent organic group represented by general formula —$R^7$— that is introduced by a reaction between a silicon-bonded hydrogen atom and an alkenyl group. Likewise, Z is preferably a divalent organic group represented by general formula —$R^7$—COO—$R^8$— that is introduced by a reaction between a silicon-bonded hydrogen atom and an unsaturated carboxylic ester group.

On the other hand, in the silylalkyl group represented by $L^i$, in which the number of generations k is 2 or more, and $L^i$ is $L^2$ to $L^k$, Z is preferably an alkylene group having from 2 to 10 carbon atoms or a divalent organic group represented by —$R^7$—COO—$R^8$— and is particularly preferably a group selected from an ethylene group, a propylene group, a methylethylene group, a hexylene group, and —$CH_2C(CH_3)COO$—$C_3H_6$—.

In the general formula described above, $R^7$ are each independently a substituted or unsubstituted straight or branched chain alkylene group or alkenylene group having from 2 to 22 carbon atoms or an arylene group having from 6 to 22 carbon atoms. More specifically, examples of $R^7$ include an ethylene group, a propylene group, a butylene group, a hexylene group, and similar straight alkylene groups; a methylmethylene group, a methylethylene group, a 1-methylpentylene group, a 1,4-dimethylbutylene group, and similar branched alkylene groups. $R^8$ is preferably a group selected from an ethylene group, a propylene group, a methylethylene group, and a hexylene group.

In the general formula described above, $R^8$ is a group selected from divalent organic groups represented by the following formula.

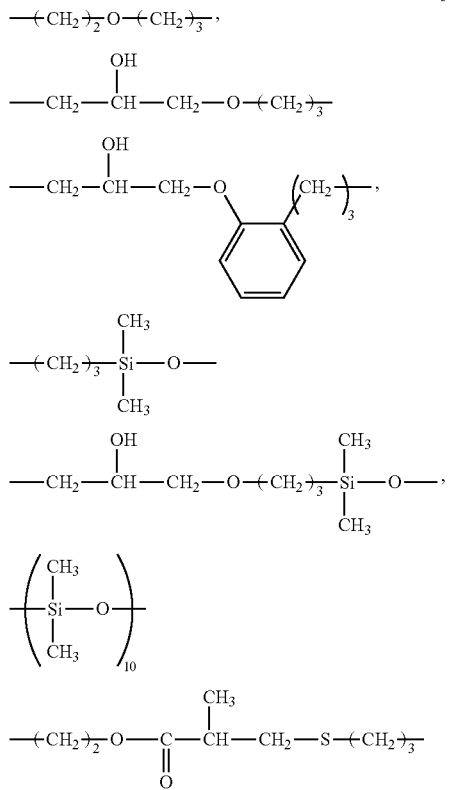

[Formula 13]

In general formula (1), Q is a glycerin derivative group, and forms the hydrophilic site of the glycerin derivative-modified silicone. The structure of Q is not limited provided that the structure has a glycerin derivative site, but the glycerin derivative residue is preferably bonded to the silicon atom via a divalent organic group.

Here, "glycerin derivative residue" refers to a hydrophilic group having a (poly)glycerin structure, and refers to a hydrophilic group having a monoglycerin, a diglycerin, a triglycerin, a tetraglycerin, and at least a pentaglycerin structure. Additionally, the terminal hydroxyl group may be partially capped with an alkyl group. Furthermore, the (poly)glycerin structure may be straight or branched, and may be a structure that is branched in a dendritic manner as well.

The glycerin derivative group (Q) described above is preferably bonded to a silicon atom via a linking group that is at least divalent, and is preferably a glycerin derivative group comprising at least one type of hydrophilic unit selected from hydrophilic units represented by structural formulae (3-3) to (3-6) below. However, the hydrophilic units constituting Q do not consist of only the following structural formula (3-6).

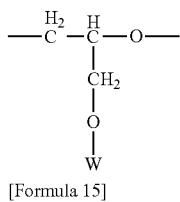

[Formula 14] (3-3)

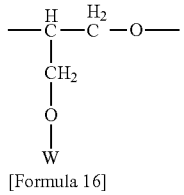

[Formula 15] (3-4)

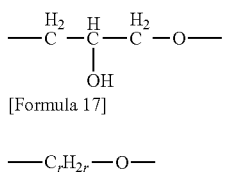

[Formula 16] (3-5)

[Formula 17]

$$—C_rH_{2r}—O—\quad (3\text{-}6)$$

In structural formula 3-1, r is a number in a range of 1 to 6.

In formulae (3-3) to (3-5), W is a hydrogen atom or an alkyl group having from 1 to 20 carbon atoms, and preferably is a hydrogen atom. Particularly, when W is a hydrogen atom, oxidation in air does not occur easily, and aldehydes such as formaldehyde and the like, and antigenic compounds such as formate esters and the like, are not easily produced over time while in storage. Therefore, when W is a hydrogen atom, there is a benefit of high environmental compatibility.

The hydrophilic units represented by structural formulae (3-3) to (3-5) are hydrophilic units included in a hydrophilic group derived from a hydrophilic compound selected principally from polyhydric alcohols including glycerin, polyglycerins (also called "polyglycerols"), and polyglycidyl ethers or compounds in which terminal hydroxyl groups thereof are partially capped by hydrocarbon groups. The glycerin derivative group (Q) pertaining to the present invention may also be a hydrophilic group containing any hydrophilic structure (polyether structure) containing oxyalkylene units represented by structural formula (3-6) (for example, oxyethylene units or oxypropylene units). However, to achieve a PEG-free formulation (a formulation not containing a compound having a polyoxyethylene (PEG) structure) as the overall formulation of a cosmetic or an external use preparation, it is preferable that the molecule not contain an oxyalkylene structure containing two or more oxyalkylene units.

In the general formula (1), Q may be, for example, a hydrophilic group that does not have a branched structure such as a monoglycerin-modified group or a diglycerin-modified group, and may also be a hydrophilic group that has a partial branched structure in the functional group such as a polyglycerol group or a polyglycidylether group.

More specifically, Q may be a glycerin derivative group bonded to a silicon atom via a linking group that is at least divalent, comprising at least one linearly bonded hydrophilic unit selected from hydrophilic units represented by the following structural formulae (3-3) to (3-6) (however, the hydrophilic units constituting Q do not consist of only the structural formula (3-6)). Similarly, Q may be a glycerin derivative group that is bonded to a silicon atom via a linking group that is at least divalent, the glycerin derivative group containing at least two hydrophilic units of at least one type selected from hydrophilic units represented by the above structural formulae (3-3) to (3-6) and having a branched unit selected from groups represented by the following structural formulae (3-7) to (3-9).

[Formula 18]

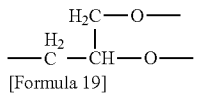
(3-7)

[Formula 19]

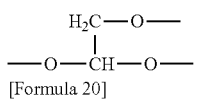
(3-8)

[Formula 20]

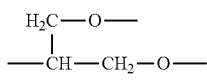
(3-9)

The at least one type of hydrophilic unit selected from the hydrophilic units represented by the general formulae (3-3) to (3-6) are each independently bonded to the two oxygen atoms of the above structural formulae (3-7) to (3-9). The hydrophilic unit may further be bonded to a branch unit selected from groups represented by structural formulae (3-7) to (3-9). Moreover, the hydrophilic unit may be formed so as to have a dendroid-shape polyether structure, a polyglycerol structure, or a polyglycidyl ether structure obtained by branching into multiple generations. For example, the structure of a hydrophilic group Q which has one branch unit represented by structural formula (3-7) and two branch units represented by structural formula (3-9) and which is branched in a dendritic manner is shown below, but it goes without saying that dendroid-shape polyglycerol structures are not limited to this example.

[Formula 21]

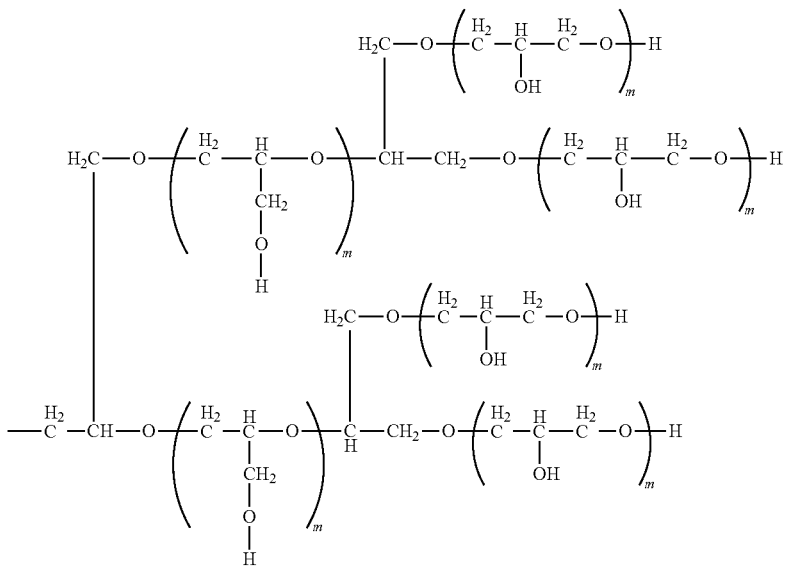

(In the formula, m is a number in a range of 0 to 50, provided that not all of the m moieties are 0).

The linking group that is at least divalent is a bonding site with respect to the silicon atom included in the hydrophilic group Q, and a structure thereof is not particularly limited. Examples thereof include, ethylene groups, propylene groups, butylene groups, hexylene groups, and similar alkylene groups; ethylene phenylene groups, propylene phenylene groups, and similar alkylene phenylene groups; ethylene benzylene groups and similar alkylene aralkylene groups; ethyleneoxy phenylene groups, propyleneoxy phenylene groups, and similar alkyleneoxy phenylene groups; methyleneoxy benzylene groups, ethyleneoxy benzylene groups, propyleneoxy benzylene groups, and similar alkyleneoxy benzylene groups; and, furthermore, groups described below. Note that there are preferably from 0 to 3 and more preferably 0 or 1 ether bonds in the linking group that is at least divalent.

[Formula 22]

More preferably, Q is a hydrophilic group represented by structural formulae (4-1) to (4-4) below, and these are generally hydrophilic groups derived from polyglycerin-based compounds.

[Formula 23]

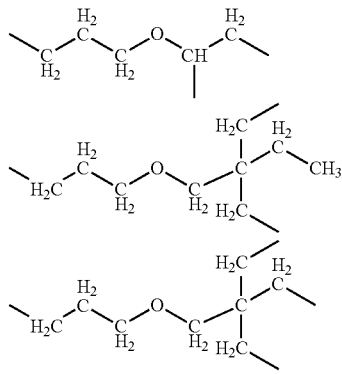

-continued

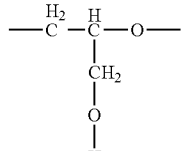

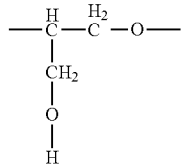

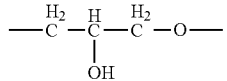

$$—R^9—(O—X^1{}_m X^2{}_q—R^{10})_p \quad (4\text{-}1)$$

$$—R^9 \left( O \begin{array}{c} H_2C—O—X^1{}_m X^2{}_q—R^{10} \\ | \\ —CH_2—CH—O—X^1{}_m X^2{}_q—R^{10} \end{array} \right)_p \quad (4\text{-}2)$$

$$—R^9 \left( O \begin{array}{c} H_2C—O—X^1{}_m X^2{}_q—R^{10} \\ | \\ —C—O—X^1{}_m X^2{}_q—R^{10} \\ | \\ H \end{array} \right)_p \quad (4\text{-}3)$$

$$—R^9 \left( O \begin{array}{c} H_2C—O—X^1{}_m X^2{}_q—R^{10} \\ | \\ —C—CH_2—O—X^1{}_m X^2{}_q—R^{10} \\ | \\ H \end{array} \right)_p \quad (4\text{-}4)$$

In formulae (4-1) to (4-4), $R^9$ is an organic group having (p+1) valence, and p is a number that is greater than or equal to 1 and less than or equal to 3. As the $R^9$, the same groups as the linking group that is at least divalent may be mentioned.

It is more preferable that p is equal to 1 and that $R^9$ is a group selected from divalent organic groups represented by the following general formulae.

[Formula 24]

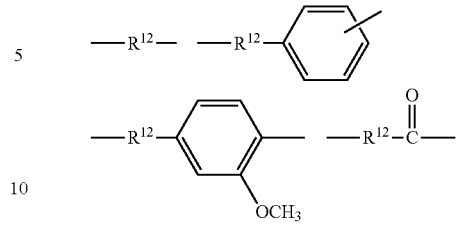

In the formulae, $R^{12}$ may have a substituent, and are each independently a straight or branched chain alkylene group or alkenylene group having from 2 to 22 carbon atoms, or an arylene group having from 6 to 22 carbon atoms.

$X^1$ are each independently at least one hydrophilic unit selected from the hydrophilic units represented by general formulae (3-3-1) to (3-5-1) below, and m is a number in a range of 1 to 5, and is more preferably a number in a range of 1 to 4.

[Formula 25]

$$—\underset{H_2}{C}—\underset{H}{C}—O— \atop \underset{\underset{\underset{H}{|}}{\underset{O}{|}}}{\underset{CH_2}{|}} \quad (3\text{-}3\text{-}1)$$

[Formula 26]

$$—\underset{H}{C}—\underset{H_2}{C}—O— \atop \underset{\underset{\underset{H}{|}}{\underset{O}{|}}}{\underset{CH_2}{|}} \quad (3\text{-}4\text{-}1)$$

[Formula 27]

$$—\underset{H_2}{C}—\underset{H}{\underset{|}{C}}—\underset{H_2}{C}—O— \atop OH \quad (3\text{-}5\text{-}1)$$

$X^2$ is any (poly)oxyethylene unit that Q may contain, and q is a number in a range of 0 to 100. q is preferably a number in a range of 0 to 50, and more preferably a range of 0 to 30. Furthermore, $X^2$ may contain a (poly)oxyethylene unit together with a (poly)oxypropylene unit and/or a (poly)oxybutylene unit. In this case, $X^2$ may also be contained in Q as a (poly)oxyalkylene unit represented by the formula: $—(C_2H_4O)_{t1}(C_3H_6O)_{t2}(C_4H_8O)_{t3}—$ (wherein t1, t2, and t3 are numbers satisfying the formulae 0≤t1≤100, 0≤t2≤100, and 0≤t3≤50, and preferably, 0≤t1≤50, 0≤t2≤50, and 0≤t3≤30, and more preferably 0≤t1≤30, 0≤t2≤30, and 0≤t3≤10). However, to achieve a PEG-free formulation as the overall formulation of a cosmetic or an external use preparation, it is preferable that the molecule not contain an oxyalkylene structure in which the average number of repetitions of the oxyalkylene unit is not less than 2.

Here, the manner in which $X^1$ and $X^2$ are bonded can be block or random. That is, the hydrophilic group Q may be a hydrophilic group in which hydrophilic segments, which are obtained by bonding hydrophilic units represented by general formulae (3-3-1) to (3-5-1) above in a block manner, are bonded to hydrophilic segments comprising polyoxyalkylene units, and may be a hydrophilic group in which these constituent units are bonded in a random manner. An example thereof is a bonding pattern such as $-(X^2)_{m1}-X^1-(X^2)_{m2}-X^1-$.

$R^{10}$ is a hydrogen atom or a group selected from the group consisting of glycidyl groups, acyl groups, and alkyl groups having from 1 to 20 carbon atoms.

From the perspectives of gel formability and the thickening effect with respect to the oil agent component of the glycerin derivative-modified silicone of the present invention and the perspective of the surface activity performance such as the emulsion and dispersion stability, a preferable hydrophilic group Q is a hydrophilic group derived from (poly)glycerin represented by the following structural formula (4-1-1).

[Formula 28]

(4-1-1)

In the formula, $R^{9'}$ is a divalent organic group, and can be a group synonymous with the group described above. $X^1$ and $R^{10}$ are synonymous with the groups described above, and m is a number in a range of 1 to 5.

In the glycerin derivative-modified silicone of the present invention, from the perspectives of thickening effect and gel formability with respect to the oil agent component, use as a surfactant (emulsifier), a moisturizer, or various treatment agents (powder dispersing agent or surface treatment agent), and particularly use as a powder treatment agent and a cosmetic composition raw material, the hydrophilic group Q is a hydrophilic group derived from a (poly)glycerin system compound and is most preferably a hydrophilic group derived from (poly)glycerin. Specifically, the hydrophilic group Q is a (poly)glycerin monoallyl ether or a (poly)glyceryl eugenol, which are examples of hydrophilic groups derived from (poly)glycerin compounds having a monoglycerin, diglycerin, triglycerin, or tetraglycerin structure.

Furthermore, in the liquid organopolysiloxane pertaining to the present invention, the glycerin derivative group is particularly preferably a diglycerin derivative group from the viewpoints of superior emulsification characteristics and superior powder dispersion characteristics, which enable the realization of a PEG-free formulation and affinity to oil agents.

A particularly preferred hydrophilic group Q is one in which the average number of repetitions m of glycerin units in the above structural formula (4-1-1) is in a range of 1.1 to 2.9, preferably in a range of 1.5 to 2.4, more preferably in a range of 1.8 to 2.2, and most preferably 2. At this time, $R^{9'}$ in the formula is a divalent organic group, which can be exemplified by the same groups as described above. $X^1$ and $R^{10}$ are also the same groups as described above. If the average number of repetitions of the hydrophilic unit is in the above range, there is the advantage that a water-in-oil emulsion composition that is stable over a long period in a wide range of oil agent systems and has small emulsified particle size can be obtained.

A diglycerin derivative group in which the number of glycerin unit repetitions, on average, is 2 is preferably contained in an amount exceeding 25 mass % of the total, relative to other glycerin derivative groups, more preferably not less than 50 mass %, and particularly preferably not less than 80 mass %. Most preferably, it is a pure product in which the purity of the diglycerin derivative groups exceeds 98 mass %. Furthermore, when the target is a PEG-free formulation, there must not be an oxyalkylene structure in which the average number of repetitions of the oxyalkylene unit in the same functional group is not less than 2.

The diglycerin derivative group is more preferably a diglycerin derivative group represented by the following structural formula (5):

(5)

In the formula, R is a divalent organic group, and is exemplified by the same divalent linking groups as described above. R is preferably a divalent linking group that does not contain an oxyalkylene structure in which the average number of oxyalkylene unit repetitions is not less than 2. X is at least one glycerin unit selected from hydrophilic units represented by structural formulae (3-3-1) to (3-5-1) below. m is the number of glycerin unit repetitions, and on average, is a number in a range of 1.5 to 2.4. The preferred ranges of the number of glycerin unit repetitions are the same as described above.

Most preferably, the diglycerin derivative group is a diglycerin derivative group represented by following general formula (5-1):

[Formula 29]

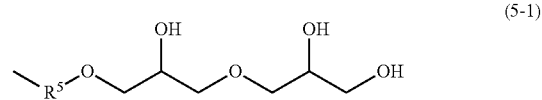

(5-1)

(In the formula, $R^5$ is a divalent organic group that does not contain an oxyalkylene structure wherein an average value of the number of repetitions of the oxyalkylene unit is two or more) or the following general formula (5-2):

[Formula 30]

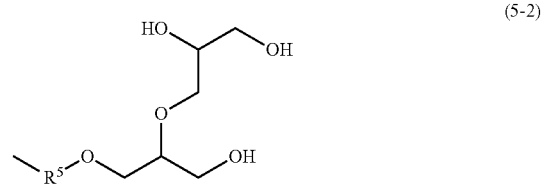

(5-2)

(In the formula, $R^5$ is synonymous with those described above.)

In the liquid organopolysiloxane pertaining to the present invention, the diglycerin derivative group is preferably a hydrophilic group derived from diglycerin monoallyl ether or diglyceryl eugenol.

The bond position of the glycerin derivative group (-Q) can be either the terminal or side chain of the polysiloxane that is the main chain; and the structure may have two or more glycerin derivative groups per molecule of glycerin derivative-modified silicone. Furthermore, the two or more glycerin derivative groups can be the same or different glycerin derivative groups. These two or more glycerin derivative groups can be structured such that bonding occurs only in a side chain of the polysiloxane that is the main chain, only at a terminal, or in a side chain and at a terminal.

The glycerin derivative-modified silicone having a glycerin derivative group (-Q) represented by general formula (1) is preferably a liquid at a temperature of at least 100° C. In addition, the polysiloxane main chain may be a straight chain, a branched chain, or reticulated (including slightly crosslinked and elastomeric). With the production method of the present invention, it is possible to easily improve the opaque appearance of a composition and stabilize the composition as a semi-transparent or transparent uniform liquid, not only in the case of a low-viscosity glycerin derivative-modified silicone, but also in the case of a glycerin derivative-modified silicone which has high viscosity and is in a solid form at room temperature (including gummy compositions having plasticity and poor fluidity).

The particularly preferable glycerin derivative-modified silicone of the present invention is a glycerin derivative-modified silicone having a straight chain polysiloxane structure represented by structural formula (1-1) below:

When $R^2$ is the long chain alkyl group, n2>1 is particularly preferable from the standpoint of compatibility with oil agents other than silicone and surface activity. n3 preferably is a number in a range of 0 to 250, and it is particularly preferable that 3>1, and that it has least one silylalkyl group ($-L^1$) having a siloxane dendron structure in a side chain portion. n4 is a number in a range of 0 to 100, and preferably is in a range of 0 to 50. However, when n4=0, at least one X needs to be Q.

In the structural formula (1-1), it is preferable that Q are each independently a glycerin derivative group represented by any of general formulae (4-1) to (4-4). In the glycerin derivative-modified silicone, all Qs can be one type of glycerin derivative group that is represented by any of general formulae (4-1) to (4-4). Some of the Qs in a molecule can be glycerin derivative groups represented by any of general formulae (4-1) to (4-4) above. The remaining Qs may be another glycerin derivative group.

[Formula 31]

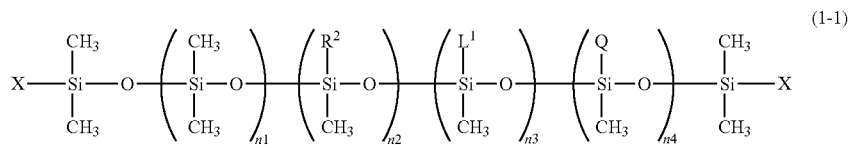

(In the formula,
$R^2$, $L^1$, and Q are each independently synonymous with those described above;
X is a group selected from the group consisting of a methyl group, $R^2$, $L^1$, and Q;
n1, n2, n3, and n4 are each independently a number in a range of 0 to 2,000, and n1+n2+n3+n4 is a number in a range of 0 to 2,000; however, when n4=0, at least one X is Q.)

In formula (1-1), (n1+n2+n3+n4) preferably is a number in a range of 10 to 2,000, more preferably is in a range of 25 to 1,500, and particularly preferably is a number in a range of 50 to 1,000. n1 preferably is a number in a range of 10 to 2,000, more preferably is in a range of 25 to 1,500, and particularly preferably is in a range of 50 to 1,000. n2 preferably is a number in a range of 0 to 250, more preferably in a range of 0 to 150.

Furthermore, the glycerin derivative-modified silicone can be a mixture of one or two or more types of a glycerin derivative-modified silicone represented by general formula (1). More specifically, the glycerin derivative-modified silicone can be a mixture of at least two types of glycerin derivative-modified silicone, with different types of modified groups, modification rate, and degree of polymerization of the siloxane main chain.

As the glycerin derivative-modified silicone, the glycerin derivative-modified silicone represented by the following structural formula (1-1-1) is preferable:

[Formula 32]

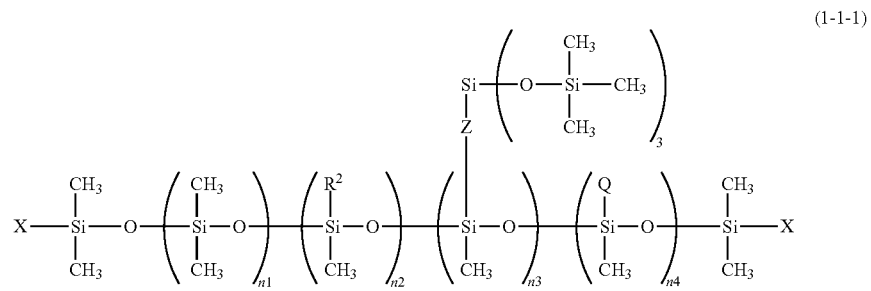

(In the formula, $R^2$, Q, X, Z, n1, n2, n3, and n4 are synonymous with those described above), or the following structural formula (1-1-2):

[Formula 33]

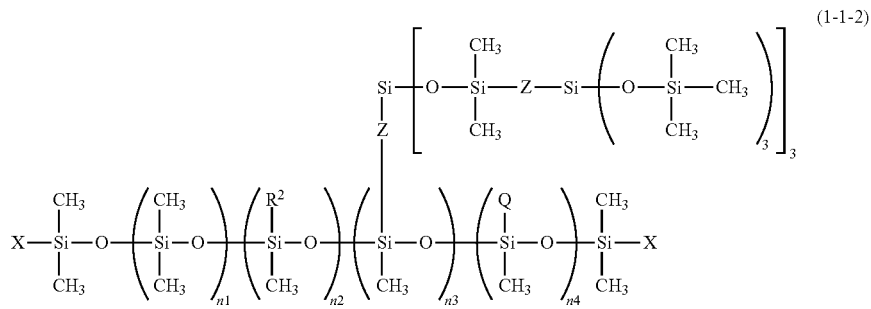

(1-1-2)

(In the formula, $R^2$, Q, X, Z, n1, n2, n3, and n4 are synonymous with those described above).

The modification rate of organopolysiloxane by the glycerin derivative group is preferably in a range of 0.001 to 50 mol %, more preferably within a range of 0.01 to 30 mol %, and yet more preferably within a range of 0.1 to 10 mol %, of all functional groups bonded to the polysiloxanes that is the main chain. Furthermore, in the glycerin derivative-modified silicone represented by structural formula (1-1), the modification rate (mol %) by the glycerin derivative group is represented by the following formula:

Modification rate(mol %)=(number of glycerin derivative groups bonded to silicon atoms per molecule)/[6+2×(n1+n2+n3+n4)]×100

For example, in the case of a glycerin derivative-modified silicone consisting of dodecylsiloxane having ten glycerin derivative group-containing organic groups (GLY groups) (represented by the structural formula $MD^{GLY}_{10}M$), 10 of the 26 silicon-bonded functional groups are modified by the glycerin derivative group-containing organic groups, so the modification rate by the glycerin derivative group-containing organic groups is 38.5 mol %.

(Production of Glycerin Derivative-Modified Silicone and Mixture Containing the Same as a Main Component)

The glycerin derivative-modified silicone can be obtained by, for example, reacting (a1) a glycerin derivative having one reactive unsaturated group per molecule, (b1) organopolysiloxane having silicon atom bonded hydrogen atoms, and (c1) an organic compound having one reactive unsaturated group per molecule, and if necessary, (d1) a siloxane dendron compound having one reactive unsaturated group per molecule, and/or (e1) a long chain hydrocarbon compound or a chain organopolysiloxane compound having one reactive unsaturated group per molecule in the presence of a hydrosilylation reaction catalyst. The reactive unsaturated group preferably is an unsaturated functional group having a carbon-carbon double bond, and is exemplified by an alkenyl group or unsaturated fatty acid ester group. The —$R^1$ is introduced by component (c1), the -$L^1$ is introduced by component (d1), and the id —$R^2$ is introduced by component (e1).

More specifically, a glycerin derivative-modified silicone can be obtained as below, for example.

The glycerin derivative-modified silicone can be obtained by addition reacting with organopolysiloxane having a silicon-hydrogen bond, an unsaturated organic compound having a carbon-carbon double bond at one terminal of the molecular chain, and an unsaturated ether compound of a glycerin derivative having a carbon-carbon double bond in the molecule. Furthermore, a siloxane dendron compound having a carbon-carbon double bond at one terminal of the molecular chain, and/or an unsaturated long chain hydrocarbon compound having a carbon-carbon double bond at one terminal of the molecular chain, or a chain organopolysiloxane having a carbon-carbon double bond at one terminal of the molecular chain can be further addition reacted.

In the above case, the glycerin derivative-modified silicone can be obtained as the product of a hydrosilylation reaction between the unsaturated organic compound and the glycerin derivative unsaturated ether compound, and arbitrarily the siloxane dendron compound and/or an unsaturated long chain hydrocarbon compound, or a chain organopolysiloxane having a carbon-carbon double bond at one terminal of the molecular chain and a SiH group-containing siloxane. This enables the introduction of an organic group and a glycerin derivative group, and optionally a silylalkyl group having a siloxane dendron structure and/or a long chain hydrocarbon group or a chain organopolysiloxane group into the polysiloxane chain of the glycerin derivative-modified silicone. This reaction can be performed as a batch or can take the form of successive reactions. However, successive reactions are preferable from the perspectives of safety and quality control.

For example, the glycerin derivative-modified silicone can be obtained by reacting at least the (b2) organohydrogensiloxane represented by the following formula (1') and (a2) a glycerin derivative having one reactive unsaturated group per molecule, in the presence of a hydro silylation reaction catalyst:

[Formula 34]

$$R^1{}_aH_{b+c+d}SiO_{(4-a-b-c-d)/2} \quad (1')$$

(wherein $R^1$, a, b, c, and d are synonymous with those described above). It is preferable to further react (d) a siloxane dendron compound having one reactive unsaturated group per molecule, and/or (e) a hydrocarbon compound having one reactive unsaturated group per molecule, or chain organopolysiloxane having one reactive unsaturated group per molecule.

The glycerin derivative-modified silicone can be preferably produced by reacting together component (a2), component (d) and/or component (e), as well as (b2) the organohydrogensiloxane represented by general formula (1'), or by successively addition reacting the (b2) organohydrogensiloxane and optionally the component (d), and/or the component (e), and further addition reacting the component (a2), in the state where (a2) a glycerin derivative having one reactive unsaturated group per molecule, and arbitrarily (d) a siloxane dendron compound having one reactive unsaturated group per molecule, and/or (e) a hydrocarbon compound having one reactive unsaturated group per molecule or a chain organopolysiloxane having one reactive unsaturated group per molecule coexist.

As (b2) an organohydrogensiloxane used in the synthesis of the glycerin derivative-modified silicone, the organohydrogensiloxane is preferably represented by, for example, the following structural formula (1-1'):

[Formula 35]

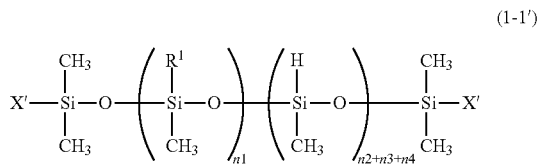

(1-1')

(wherein
$R^1$ are each independently synonymous with that described above;
X' is a group selected from $R^1$ or hydrogen atom; and
n1, n2, n3, and n4 are synonymous with those described above; however, when n2+n3+n4=0, at least one X' is a hydrogen atom)

The glycerin derivative-modified silicone is preferably synthesized by subjecting to a hydrosilylation reaction (a) a glycerin derivative having a carbon-carbon double bond at a terminal of the molecular chain, and (b) an organohydrogenpolysiloxane; and the organohydrogensiloxane (component (b)) is preferably the organohydrogensiloxane obtained by successively addition reacting the component (d1) and/or the component (e1). In this case, the organohydrogensiloxane immediately prior to reaction with component (a) (after successive reactions with other components) is preferably represented by the following structural formula (1-1A).

[Formula 36]

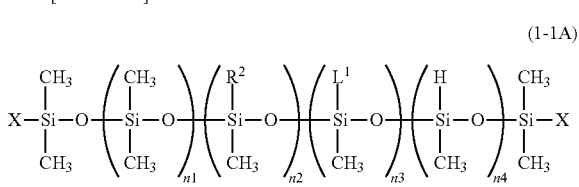

(1-1A)

(wherein
$R^2$ and $L^1$ are each independently synonymous with those described above;
X is selected from the group consisting of a methyl group, $R^2$, $L^1$, and a hydrogen atom (H);
n1, n2, n3, and n4 are each independently a number in a range of 0 to 2,000, and n1+n2+n3+n4 is a number in a range of 0 to 2,000; however, when n4=0, at least one X is a hydrogen atom.)

A glycerin derivative having one reactive unsaturated group per molecule, which is used in the synthesis of the glycerin derivative-modified silicone, is preferably (a) a glycerin derivative having a carbon-carbon double bond at the terminal of molecular chain. This is a (poly)glycerin derivative having an allyl(poly)glycerin, allyl polyglycidyl ether, (poly)glycerin monoallyl ether, or similar reactive functional group having an alkenyl group or the like at the molecular terminal, and can be synthesized according to a publicly known method.

In the glycerin derivative-modified silicone of the present invention, from the perspectives of thickening effect and gel formability with respect to an oil agent, use as a surfactant (emulsifier), and various treatment agents (powder dispersing agents or surface treatment agents), component (a) is specifically a (poly)glycerin monoallyl ether or a (poly) glyceryl eugenol, of which examples are (poly)glycerin compounds having a monoglycerin, a diglycerin, a triglycerin, or a tetraglycerin structure.

Such a component (a) can be exemplified by a glycerin derivative having a carbon-carbon double bond at the terminals of the molecular chain shown by the following structural formulae (4-1') through (4-4'). In the formulae, $X^1$, $X^2$, and $R^{10}$ are groups synonymous with the groups described above, and m and q are numbers synonymous with the numbers described above. R' is an unsaturated organic group having a carbon-carbon double bond at the terminal, and is preferably a substituted or unsubstituted, straight or branched unsaturated hydrocarbon group having from 3 to 5 carbon atoms. Examples of the unsaturated hydrocarbon group having from 3 to 5 carbon atoms include allyl groups, butenyl groups, methallyl groups, and similar alkenyl groups; and the unsaturated hydrocarbon group is preferably an allyl group.

[Formula 37]

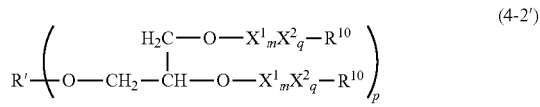

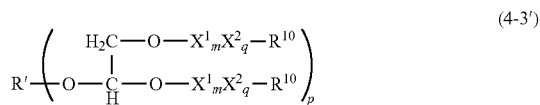

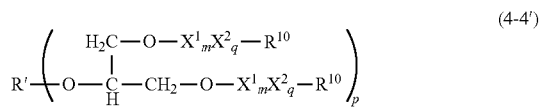

(d) The siloxane dendron compound that has one reactive unsaturated group per molecule used in the synthesis of a glycerin derivative-modified silicone of the present invention, is preferably a compound having a siloxane dendron structure with one carbon-carbon double bond at a molecular terminal, and is represented by the following general formula (3'):

[Formula 38]

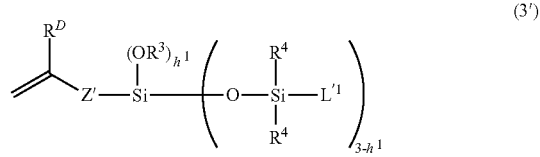

In this formula:
$R^3$ and $R^4$ are synonymous with those described above, $R^D$ is a hydrogen atom or a methyl group;
Z' is a divalent organic group;
$h^1$ is a number in a range of 0 to 3;

$L^{j1}$ is the $R^4$ moiety or, when j=1, a silylalkyl group represented by general formula (3″) below:

[Formula 39]

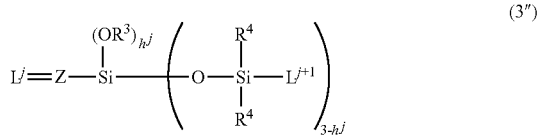

(wherein $R^3$ and $R^4$ are synonymous with those described above;
Z is a divalent organic group;
j indicates the generations of the silylalkyl group that is represented by $L^j$, when the number of generations (the number of repetitions) of the silylalkyl group is k', j is an integer from 1 to k', and the number of generations k' is an integer from 1 to 9; $L^{j+1}$ is the silylalkyl group when j is less than k' and is the $R^4$ moiety when j=k'; and
$h^j$ is a number in a range of 0 to 3).

(e) The hydrocarbon compound having one reactive unsaturated group per molecule or chain organopolysiloxane having one reactive unsaturated group per molecule used in the synthesis of a glycerin derivative-modified silicone of the present invention, is preferably a mono unsaturated organic compound represented by the following general formula (2'):

[Formula 40]

(wherein R' is synonymous with that described above; and $R^{2'}$ represents a substituted or unsubstituted, straight or branched monovalent hydrocarbon group having from 7 to 58 carbon atoms) or the following general formula (2-1):

[Formula 41]

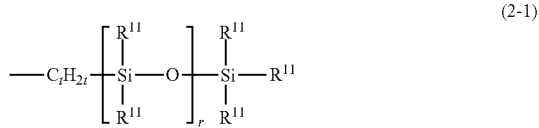

(wherein $R^{11}$, t, and r are synonymous with those described above); or the following general formula (2-2):

[Formula 42]

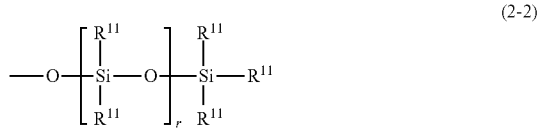

(wherein $R^{11}$ and r are synonymous with those described above).

The hydrocarbon compound having one reactive unsaturated group in the molecule (e) is preferably a monounsaturated hydrocarbons having from 9 to 30 carbon atoms and is more preferably a 1-alkene. Examples of the 1-alkene include 1-nonene, 1-decene, 1-undecene, 1-dodecene, 1-tridecene, 1-tetradecene, 1-hexadecene, 1-octadecene and the like. Examples of the chain organopolysiloxane having one reactive unsaturated group in the molecule include a dimethylpolysiloxane capped at one molecular terminal with a vinyl group, a methylphenylpolysiloxane capped at one molecular terminal with a vinyl group, and the like.

The hydrosilylation reaction used to synthesize the glycerin derivative-modified silicone or the composition thereof can be carried out using a publicly known method in the presence or absence of a solvent. Here, examples of the reaction solvent include alcohol-based solvents such as ethanol and isopropyl alcohol; aromatic hydrocarbon-based solvents such as toluene and xylene; ether-based solvents such as dioxane and THF; aliphatic hydrocarbon-based solvents such as n-hexane, cyclohexane, n-heptane, cycloheptane, and methylcyclohexane; and chlorinated hydrocarbon-based organic solvents such as carbon tetrachloride.

The hydrosilylation reaction may be performed in the absence of a catalyst, but preferably is performed in the presence of a catalyst because the reaction can be carried out at a low temperature and in a shorter period of time. Examples of the catalyst include platinum, ruthenium, rhodium, palladium, osmium, iridium, and similar compounds, and platinum compounds are particularly effective due to their high catalytic activity. Examples of the platinum compound include chloroplatinic acid; platinum metal; platinum metal supported on a carrier such as platinum supported on alumina, platinum supported on silica, platinum supported on carbon black, or the like; and a platinum complex such as platinum-vinylsiloxane complex, platinum-phosphine complex, platinum-phosphite complex, platinum alcoholate catalyst, or the like. If a platinum catalyst is used, the usage quantity of the solvent is approximately from 0.0001 to 0.1 wt. %, and preferably from 0.0005 to 0.05 wt. %, relative to the weight of the metal catalyst, but is not particularly limited.

A reaction temperature of the hydrosilylation reaction is typically from 30 to 120° C., and a reaction time is typically from 10 minutes to 24 hours and preferably from 1 to 10 hours.

When the hydrosilylation reaction is performed, the ratio [amount of substance of carbon-carbon double bonds in glycerin derivative group-containing compound/amount of substance of silicon-bonded hydrogen atoms to be added to the carbon-carbon double bonds of the glycerin derivative group-containing compound in the organohydrogenpolysiloxane] is preferably in a range of 0.8 to 1.5, and more preferably in a range of 1.0 to 1.3. That is, when synthesizing a glycerin derivative-modified silicone or a glycerin derivative-modified silicone-containing composition of the present invention, it is more preferable to use a slight excess of glycerin derivative group-containing compound. Although processing with the ratio above 1.5 is also possible, the proportion of residual starting material increases, so it is not economical. In addition, during the hydrosilylation reaction, the terminal carbon-carbon double bonds in the glycerin derivative group-containing compound transition internally so that a deactivating side-reaction occurs simultaneously. Therefore, when the ratio described above is from 0.8 to 1.0, the silicon-bonded hydrogen atoms consumed by the hydrosilylation reaction settle to within a slightly lower range than the range of theoretical values from 0.8 to 1.0, so silicon-bonded hydrogen atoms remain at a slightly greater ratio than 0 to 0.2. However, it is also possible to cause dehydrogenation reactions with hydroxyl groups contained in the glycerin derivative group and alcoholic hydroxyl groups of the reaction solvent, which can consume the remaining silicon-bonded hydrogen atoms, depending on the reaction conditions.

On the other hand, if the ratio is less than 0.8, there is a risk that unreacted organohydrogenpolysiloxane will remain. When such a glycerin derivative-modified silicone or a glycerin derivative-modified silicone-containing composition is used as the starting material for an external use preparation or a cosmetic composition, residual organohydrogenpolysiloxane might react with the other raw materials, and generate hydrogen gas. This might cause such undesirable effects as alteration of the external use preparation or the cosmetic composition at the incorporation destination, fire, container expansion, and the like. In addition, when an attempt is made to consume the remaining silicon-bonded hydrogen atoms by using a dehydrogenation reaction when the ratio is less than 0.8, the proportion of Si—O—C crosslinked bonds increases, which increases the tendency to cause gelation during production. Therefore, to enable the complete and safe consumption of organohydrogenpolysiloxane, it is preferable that the ratio exceeds 0.8, i.e., that 0.8 equivalent or more of the glycerin derivative group-containing compound is reacted.

[Hydration Step]

The method for producing a transparent or semi-transparent liquid glycerin derivative-modified silicone composition pertaining to the present invention includes a hydration step of adding water to a liquid glycerin derivative-modified silicone or composition thereof.

The added amount of water in the hydration step is not particularly limited but may be from 0.1 to 10 parts by mass, preferably from 0.2 to 5 parts by mass, and even more preferably from 0.5 to 3 parts by mass per 100 parts by mass of the liquid glycerin derivative-modified silicone or composition thereof. It is preferably the amount at which the composition after mixing to homogenize exhibits the maximum value (peak value) of light transmittance. In the vicinity of the optimal added amount of water, the composition becomes a homogenous liquid having a transparent or semi-transparent appearance and the stability of the composition is best at the temperature in which the composition is in the state of liquid.

The water used in the production method of the present invention must be clean and free of components that are harmful to the human body, and examples thereof include tap water, purified water, mineral water, and deep sea water. Water may be added in a range of 0.09 to 9 wt. %, preferably of 0.1 to 5 wt. %, and more preferably of 0.4 to 3 wt. % of the entire composition after hydration.

In the hydration step, the liquid glycerin derivative-modified silicone or composition thereof and the water are preferably mixed to homogenize.

Mixing to homogenize is preferably performed using mechanical power. For example, mixing can be performed with a paddle mixer, a propeller mixer, or in a reaction vessel or a container equipped with mixing blades, and an emulsifier, a kneader, or the like may also be used as necessary. Furthermore, mixing to homogenize does not necessarily have to be performed at room temperature, and the temperature may be increased or decreased in accordance with the composition, fluidity, and the like. It is normally preferable to perform mixing to homogenize within a range of 0 to 70° C. Furthermore, the same is true for mixing to homogenize the glycerin derivative-modified silicone or composition thereof and the liquid oil agent to be described later in order to obtain the glycerin derivative-modified silicone composition pertaining to the present invention.

The visible light transmittance of the transparent or semi-transparent liquid glycerin derivative-modified silicone composition after the hydration step is preferably not less than 50%, more preferably not less than 70%, and even more preferably not less than 80%. The visible light transmittance of the liquid glycerin derivative-modified silicone composition before the hydration step is preferably less than 50%, more preferably less than 25%, and even more preferably less than 5%. Light of wavelength from 360 to 830 nm is preferred as the visible light, and light of wavelength from 400 to 760 nm is more preferred. For example, light of wavelength 750 nm may be used. An optical path length of 1 to 30 mm is preferred for transmittance measurement, and an optical path length of 5 to 20 mm is more preferred. For example, the transmittance measurement may be performed with an optical path length of 10 mm. Light transmittance of the transparent or semi-transparent liquid glycerin derivative-modified silicone composition after the hydration step obtained by the present invention, particularly when measured with an optical path length of 10 mm using light of wavelength 750 nm, is preferably not less than 50%, more preferably not less than 70%, and even more preferably not less than 80%. Such a glycerin derivative-modified silicone composition is visually transparent or semi-transparent and exhibits a substantially transparent appearance.

The content of glycerin derivative-modified silicone in the transparent or semi-transparent liquid glycerin derivative-modified silicone composition after the hydration step is not particularly limited, but is preferably from 50 to 99.99 wt. %, more preferably from 70 to 99.9 wt. %, and even more preferably from 90 to 99 wt. %, based on the total weight of the composition.

[Liquid Oil Agent Addition Step]

The production method of the present invention may further comprise, before and/or after and/or simultaneously with the hydration step, a liquid oil agent addition step of adding a liquid oil agent to the liquid glycerin derivative-modified silicone or composition thereof. Here, "liquid" has the same meaning as previously described.

The liquid oil agent and the liquid glycerin derivative-modified silicone preferably have affinity. The liquid oil agent is preferably one or more oil agents selected from silicone oils, non-polar organic compounds, and low-polarity to high-polarity organic compounds that are liquid at 5 to 100° C., and the non-polar organic compounds and low-polarity to high-polarity organic compounds are preferably hydrocarbon oils, fatty acid ester oils, and liquid fatty acid triglycerides. These are components that are particularly widely used as base materials for cosmetic compositions, but it is possible to additionally use one or more types of compound selected from among publicly known vegetable oils and fats, animal oils and fats, higher alcohols, fatty acid triglycerides, artificial sebum and fluorine-based oils as well as these oil agents. Because the composition containing glycerin derivative-modified silicone modified by a glycerin derivative of the present invention exhibits excellent miscibility and dispersibility in these non-silicone-based oil agents, hydrocarbon oils and fatty acid ester oils may be stably blended into cosmetics and the moisture retention characteristics of these non-silicone-based oil agents can be leveraged. Therefore, a composition containing the above glycerin derivative-modified silicone modified by a glycerin derivative can improve the blending stability of these non-silicone-based oil agents in cosmetics.

By combining the hydrocarbon oil and/or the fatty acid ester oil with the silicone oil, in addition to the dry tactile sensation unique to silicone oils, moisture will be retained on the skin and a moisturizing feel whereby the skin or hair feels moisturized (also referred to as a luxurious tactile sensation) and smooth tactile sensation can be imparted to the cosmetic composition of the present invention. Moreover, there is a benefit in that stability over time of the cosmetic composition will not be negatively affected. Furthermore, with a cosmetic composition comprising the hydrocarbon oil and/or the fatty acid ester oil and the silicone oil, these moisturizing components (the hydrocarbon oil and/or the fatty acid ester oil) can be applied on the skin or hair in a more stable and uniform manner. Therefore, the moisturizing effects of the moisturizing components on the skin are improved. Thus, compared to a cosmetic composition comprising only a non silicone-based oil agent (e.g. a hydrocarbon oil, a fatty acid ester oil, or the like), the cosmetic composition comprising a non silicone-based oil agent along with a silicone oil is advantageous in that a smoother, more luxurious tactile sensation is imparted.

These oil agents are the same as those disclosed in paragraphs 0130 to 0135 and paragraph 0206 and the like of Patent Document 11 (WO/2011/049248) by the applicants. Examples of the fluorine-based oil include perfluoropolyether, perfluorodecalin, perfluorooctane, and the like.

The added amount of liquid oil agent in the liquid oil agent addition step is not particularly limited but may be from 5 to 1000 parts by mass, preferably from 10 to 500 parts by mass, and even more preferably from 50 to 200 parts by mass per 100 parts by mass of the liquid glycerin derivative-modified silicone or composition thereof.

In the liquid oil agent addition step, the liquid glycerin derivative-modified silicone or composition thereof and the liquid oil agent are preferably mixed to homogenize as described above.

Unlike conventional polyether-modified silicone and the like, the glycerin derivative-modified silicone composition of the present invention is stable, inherently having little tendency to degrade due to oxidation by oxygen in the air. Therefore, there is no need for the operation of increasing oxidative stability by blending antioxidants such as phenols, hydroquinones, benzoquinones, aromatic amines, or vitamins in order to prevent oxidative degradation. However, stability improves further when such antioxidants, for example, BHT (2,6-di-t-butyl-p-cresol), vitamin E, and the like are added. In this case, the added amount of the antioxidant that is used is in a range (by weight (mass)) of 10 to 1,000 ppm, and preferably of 50 to 500 ppm, of the glycerin derivative-modified silicone.

The visible light transmittance of the transparent or semi-transparent liquid glycerin derivative-modified silicone composition after the liquid oil agent addition step is preferably not less than 50%, more preferably not less than 70%, and even more preferably not less than 80%. Light of wavelength from 360 to 830 nm is preferred as the visible light, and light of wavelength from 400 to 760 nm is more preferred. For example, light of wavelength 750 nm may be used. An optical path length of 1 to 30 mm is preferred for transmittance measurement, and an optical path length of 5 to 20 mm is more preferred. For example, the transmittance measurement may be performed with an optical path length of 10 mm. Particularly when measured with an optical path length of 10 mm using light of wavelength 750 nm, light transmittance is preferably not less than 50%, more preferably not less than 70%, and even more preferably not less than 80%.

The content of glycerin derivative-modified silicone in the transparent or semi-transparent liquid glycerin derivative-modified silicone composition after the liquid oil agent addition step is not particularly limited, but is preferably from 10 to 99 wt. %, more preferably from 40 to 95 wt. %, and even more preferably from 80 to 90 wt. %, based on the total weight of the composition.

(Acid Treatment and Odor Reduction of Glycerin Derivative-Modified Silicone or Composition Thereof)

In the production method of the present invention, it is possible to obtain a glycerin derivative-modified silicone or composition thereof of even higher quality when the glycerin derivative-modified silicone or composition (mixture) thereof is treated with an acidic aqueous solution, and water and odor-causing substances produced by treatment with the acidic aqueous solution are removed by heating or depressurization.

The acidic substance contained in the acidic aqueous solution can be selected optionally, but it is optimal to use one or more types of acidic inorganic salts which are solids at 25° C., are water-soluble, and have an aqueous solution pH of at most 4 at 25° C. when 50 g is dissolved in 1 L of ion exchanged water.

Furthermore, treatment using the acidic aqueous solution can be most preferably performed when the glycerin derivative-modified silicone is synthesized by a hydrosilylation reaction. Therefore, the case of a glycerin derivative-modified silicone synthesized by a hydrosilylation reaction will be described hereinafter as an example of an acid treatment and odor reducing method for a glycerin derivative-modified silicone and a mixture containing the same.

Acid Treatment Preferably Includes:
a process (V) of synthesizing a glycerin derivative-modified silicone or a reaction mixture containing the same as a main component by performing a hydrosilylation reaction on: (ax) a glycerin derivative having carbon-carbon double bonds at the terminals of the molecular chain; and
(bx) an organohydrogenpolysiloxane; and
together with the synthesis process (V) or after the synthesis process (V),
a process (W) of treating the glycerin derivative-modified silicone or a reaction mixture containing the same as a main component
in the presence of at least one type of acidic inorganic salts which are solids at 25° C., are water-soluble, and have an aqueous solution pH of at most 4 at 25° C. when 50 g is dissolved in 1 L of ion exchanged water.

In addition, because a treatment process that uses the acidic inorganic salt involves the generation of odor-causing substances it is more preferable to include a process of removing odor-causing substances by heating or depressurizing after process (W), from the perspective of odor reduction effectiveness.

For example, in process (V), when the hydrosilylation reaction is performed using (ax) a glycerin derivative such as (poly)glycerin monoallyl ether and (bx) a straight-chain organohydrogenpolysiloxane represented by the structural formula (1-1A) in amounts so that there is an excessive amount of the substance of the component (ax) with respect to the silicon-bonded hydrogen atoms in the component (bx), the glycerin derivative-modified silicone represented by the structural formula (1-1) is synthesized, and a crude product of a reaction mixture containing the glycerin derivative-modified silicone and the unreacted component (ax) and containing the glycerin derivative-modified silicone as a main component is obtained.

Process (W) is a process for efficiently reducing the odors of the composition highly effectively and effectively suppressing the generation of odors over time by hydrolyzing the crude product using specific acidic inorganic salts, with practically no breakage of the silicon-oxygen bonds forming the main chain of polysiloxane or the carbon-oxygen bonds of side chain portions.

Process (W) specifically removes odor-causing substances from the crude product of the reaction mixture containing the glycerin derivative-modified silicone as a main component by using hydrolysis, and it is characterized by performing treatment in the presence of one or more types of acidic inorganic salts which are solids at 25° C., are water-soluble, and have an aqueous solution pH of at most 4 at 25° C. when 50 g is dissolved in 1 L of ion exchanged water. Note that pH values in the present invention are values that are measured using a pH meter having a glass electrode in a sample aqueous solution at room temperature (25°). In the present application, HM-10P produced by DKK-TOA Corporation was used for the pH measurement.

The acidic inorganic salt serving as a component (cx) needs to be a solid at 25°, needs to be water-soluble, and the aqueous solution needs to have a pH of at most 4 when 50 g of the acidic inorganic salt is dissolved in 1 L of ion exchanged water. The pH is preferably at most 3.5 and particularly preferably at most 2.0. By using such a water-soluble acidic inorganic salt for hydrolysis treatment of the composition, it is possible to reduce odors in the composition highly effectively and suppress odorization over time effectively, with almost no breakage of C—O bonds or Si—O bonds.

Examples that can be used as the acidic inorganic salt include acidic inorganic salts in which at least a monovalent hydrogen atom of the inorganic acid that is at least divalent is neutralized by a base. Examples of the inorganic acid that is at least divalent include sulfuric acid, sulfurous acid, and the like. Examples of the base include an alkali metal, ammonia, and the like.

More specifically, the component (cx) is preferably at least one type of acidic inorganic salt comprising a hydrogensulfate ion ($HSO_4^-$) or a hydrogensulfite ion ($HSO_3^-$) and a monovalent cation ($M^+$). Examples of the monovalent cation ($M^+$) include alkali metal ions or an ammonium ion. Particularly, the monovalent cation is preferably at least one type selected from the group consisting of a sodium ion, a potassium ion, and an ammonium ion. Additionally, one type of the acidic inorganic salt may be used alone or two or more types of acidic inorganic salt may be used. Furthermore, the acidic inorganic salt can be easily removed via filtration because the acidic inorganic salt is solid at room temperature (25° C.). Additionally, because it is water soluble, the acidic inorganic salt can be easily rinsed off using water, even in the cleaning process after production.

On the other hand in hydrolysis treatment based on an acetic acid salt, phosphoric acid salt, and the like that does not satisfy the conditions of the component (cx), it is impossible to sufficiently reduce the odor of the composition after hydrolysis. On the other hand, in hydrolysis treatment based on a strong acid such as hydrochloric acid and the like, and in hydrolysis treatment based on a publicly known solid acid of zirconium sulfate and the like, the odor can be reduced by a certain amount, but C—O bonds and Si—O bonds of the composition break easily at the time of hydrolysis.

Specific examples of the acidic inorganic salt serving as the component (cx) are lithium hydrogensulfate, sodium hydrogensulfate, potassium hydrogensulfate, rubidium hydrogensulfate, cesium hydrogensulfate, ammonium hydrogensulfate, sodium hydrogensulfite, or hydrates thereof. The pH of aqueous solutions in which 50 g of the acidic inorganic salt is dissolved in 1 L of ion exchanged water is as shown in Table below. From the perspective of the technical benefit of reducing odor, the water soluble acidic inorganic salt having a pH of not higher than 2.0 is most preferably at least one type of acidic inorganic salt selected from the group consisting of sodium hydrogensulfate, potassium hydrogensulfate, and ammonium hydrogensulfate.

TABLE 1

| Acidic inorganic salt | pH (50 g/L) |
| --- | --- |
| Sodium hydrogensulfate | 1.5 or lower |
| Potassium hydrogensulfate | 2.0 or lower |
| Ammonium hydrogensulfate | 1.5 or lower |
| Sodium hydrogensulfite | 3.5 |

For example, treatment in the presence of an acidic inorganic salt refers to (1) decomposition treatment involving adding and stirring the acidic inorganic salt into the reaction system (for example, a reaction vessel such as a flask) of the reaction mixture containing the glycerin derivative-modified silicone synthesized by a hydrosilylation reaction as a main component, and (2) hydrolysis treatment or the like involving adding and stirring an acidic inorganic salt and water or an acidic inorganic salt, water, and a hydrophilic solvent. The treatment process that uses the acidic inorganic salt is preferably carried out in the presence of at least one of water and a hydrophilic solvent.

A particularly preferable hydrolysis treatment is a hydrolysis treatment whereby, after the process (V), at least an acidic inorganic salt and water are added to a reaction system containing a crude product of the reaction mixture containing the glycerin derivative-modified silicone as a main component, and depending on the case, another hydrophilic solvent is further added with the objective of increasing the treatment efficiency by improving computability, and the solution is further stirred using a mechanical force. The hydrolysis treatment can be carried out at any temperature and treatment time, and can be carried out at a temperature from 0 to 200° C. and more preferably from 50 to 100° C. for a reaction time of from 0.1 to 24 hours and more preferably from about 0.5 to 10 hours. The amount of the acidic inorganic salt that is used can be selected appropriately in accordance with the treatment apparatus and the treatment time. However, the amount is preferably within a range of 50 to 10,000 ppm and more preferably within a range of 100 to 5,000 ppm with respect to the reaction mixture containing the glycerin derivative-modified silicone as a main component.

After the acid treatment described above, it is preferable to include a stripping process in which low-boiling-point components (propionaldehyde and the like), which are odor-causing substances, are removed. In addition, after stripping, it is possible to hydrolyze more of the propenyl ether group-containing glycerin derivative or the like by treating again in the presence of an acidic inorganic salt, and propionaldehyde and the like, which are odor-causing substances, can be removed. At this time, there is an advantage that, because acidic inorganic salt remains, an acidic inorganic salt need not be newly added. Therefore, it is only necessary to add a hydrophilic solvent, typified by water. That is, the aforementioned process [W] and the stripping process can be repeated two times or more, to increase the degree of odor reduction, or the like.

Furthermore, the "materials with a low boiling point" which are distilled off by the stripping process, include not only propionaldehyde which is an odor-causing substance, but also the reaction solvents used in the hydrosilylation reaction (process [V]), the water used in the odor reduction treatment process, hydrophilic solvents, and the like.

The stripping process (removal of low-boiling-point substances) may be performed on the crude product of the reaction mixture containing the glycerin derivative-modified silicone as a main component as the process preceding process (W), or may be performed on the reaction mixture containing the glycerin derivative-modified silicone as a main component as the process following process (W). In addition, the stripping process can be performed as the pre processing and post processing of process [W]. The stripping process is preferably performed after the process [W], to remove propionaldehyde, which is an odor-causing substance generated by the hydrolysis reaction.

As the removal method, stripping under normal pressure or under reduced pressure is preferable, and stripping at a temperature of 120° C. or lower is preferable. In order to effectively perform the stripping, the stripping is preferably performed under reduced pressure or, for example, performed under a nitrogen gas or similar inert gas stream. A specific example of the operation for removing low-boiling-point matter is one in which a crude product of the reaction mixture containing the glycerin derivative-modified silicone containing the low-boiling-point matter as a main component is placed in a flask having a refluxing cooler, a nitrogen injection port, or the like; and, while supplying nitrogen gas, the internal pressure is reduced, and the internal temperature is increased and the pressure and temperature are maintained so as to be constant. Thus, the light matter is removed. Here, typically, a pressure reduction parameter is from 0.1 to 10.0 kPa, a heating temperature is from 40 to 120° C., and a treatment time is from 10 minutes to 24 hours.

Furthermore, after the acid treatment process, a basic substance may be used to neutralize the reaction mixture containing the glycerin derivative-modified silicone as a main component. Examples of the basic substance include sodium hydroxide, potassium hydroxide, calcium hydroxide, barium hydroxide, ammonia water, sodium hydrogen carbonate, and similar inorganic salt groups; various amines, basic amino acids, and similar organic bases; and the like. The amount of the basic substance is preferably an amount needed to neutralize a reaction system comprising the reaction mixture containing the glycerin derivative-modified silicone as a main component but, as necessary, the amount of the basic substance may be adjusted to an amount by which weak acidity or weak alkalinity is obtained.

In addition, an alkaline buffer may be further added in an amount corresponding to from 100 ppm to 50,000 ppm to the reaction mixture containing the glycerin derivative-modified silicone obtained after the acid treatment process as a main component. A minute amount of acid may be locally dissolved in the reaction mixture containing the glycerin derivative-modified silicone as a main component even after a neutralization or filtration process. By adding an alkaline buffer, the liquidity of the cosmetic or the like into which the glycerin derivative-modified silicone is blended is maintained on the alkali side, which makes it possible to reduce the risk of odorization caused by the impurities of the glycerin derivative-modified silicone. A useful alkaline buffer is not particularly limited as long as the alkaline buffer comprises a combination of a strong base and a weak acid. Examples of the alkaline buffer include trisodium phosphate, tripotassium phosphate, trisodium citrate, sodium acetate, and other alkaline buffers. Furthermore, these alkaline buffers may be added to a cosmetic composition starting material or the like comprising a glycerin derivative-modified silicone or a mixture containing the same as a main component, or they may be added to a composition at the preparation stage or after the blending of a glycerin derivative-modified silicone or cosmetic composition that contains another cosmetic composition raw material or water. By so doing, odor production during formulation or over time can be more effectively suppressed.

The glycerin derivative-modified silicone or the mixture containing the same as a main component can also be subjected to hydrogenation treatment as a process before or after treatment in the presence of an acidic inorganic salt in process (W). A deodorizing treatment using a hydrogenation reaction may be performed after treatment in the presence of the acidic inorganic salt of the process (W). On the other hand, the treatment in the presence of the acidic inorganic salt of the process (W) may be performed after deodorizing treatment using a hydrogenation reaction. However, hydrogenation treatment may generally lead to an increase in the cost of the product.

A second aspect of the present invention is an external use preparation, a cosmetic, or an industrial material containing the glycerin derivative-modified silicone composition obtained by the production method of the present invention.

<External Use Preparation/Cosmetic>

The glycerin derivative-modified silicone composition obtained by the production method of the present invention can be suitably blended into an external use preparation or a cosmetic and can form the external use preparation or cosmetic of the present invention. In addition, it is also possible to produce a raw material for external use preparations and cosmetics containing the glycerin derivative-modified silicone composition obtained by the production method of the present invention and to blend the raw material into an external use preparation or a cosmetic.

In particular, because the glycerin derivative-modified silicone composition obtained by the production method of the present invention has high transparency and has transparency that is stable regardless of temperature environment, it can be advantageously blended in external use preparations or cosmetics that require a transparent or semi-transparent appearance. Additionally, because the glycerin derivative-modified silicone composition obtained by the production method of the present invention has stable viscosity regardless of temperature environment, it is superior in ease of handling, and can stabilize the viscosity of an external use preparation or cosmetic in which it is blended. Moreover, the glycerin derivative-modified silicone composition obtained by the production method of the present invention has a low degree of odor and produces practically no odor during formulation or over time. Moreover, there is the advantage of breaking almost no silicon-oxygen bonds which may form the main chain of the glycerin derivative-modified silicone and the carbon-oxygen bonds which may form the side chains. Therefore, the glycerin derivative-modified silicone composition obtained by the production method of the present invention can be suitably used as a raw material for external use preparations and cosmetics used on the human body.

The proportion of the glycerin derivative-modified silicone composition in the raw material for an external use preparation or a cosmetic is preferably from 10 to 100 wt. % (mass %), more preferably from 20 to 100 wt. % (mass %), and even more preferably from 30 to 100 wt. % (mass %) relative to the total weight (mass %) of the raw material. The proportion of the raw material compounded in the external use preparation or the cosmetic composition is not particularly limited but, for example, can be from 0.1 to 40 wt. %

(mass %), and is preferably from 1 to 30 wt. % (mass %), more preferably from 2 to 20 wt. % (mass %), and even more preferably from 3 to 10 wt. % (mass %) relative to the total weight (mass) of the external use preparation or the cosmetic composition.

The glycerin derivative-modified silicone composition obtained by the production method of the present invention can be applied to applications common to the co-modified organopolysiloxanes described in Patent Document 11 (WO/2011/049248), Patent Document 12 (WO/2011/049247), and Patent Document 14 (Japanese Unexamined Patent Application Publication No. 2012-046507A), or the novel organopolysiloxane copolymer described in Patent Document 13 (WO/2011/049246). In addition, the glycerin derivative-modified silicone composition obtained by the production method of the present invention can be used in the same manner as the co-modified organopolysiloxanes described in Patent Documents 11, 12, and 14 and the novel organopolysiloxane copolymer described in Patent Document 13 with regard to combinations with any cosmetic raw material components, external use preparations, and, in particular, formulations, types, and formulation examples of cosmetics, and can be blended into various cosmetics or the like.

The external use preparation of the present invention is not particularly limited, provided that it is a composition applied to the human body as a cosmetic or a medicament. Specific examples of cosmetic composition products of the present invention include skin cleansing agent products, skin care products, makeup products, anti-perspirant products, ultraviolet light blocking products, and similar skin use cosmetic products; hair use cleansing agent products, hair dressing products, hair use coloration products, hair growth products, hair rinsing products, hair conditioning products, hair treatment products, and similar hair use cosmetic products; and bath use cosmetic products. Examples of the medicament of the present invention include hair regrowth agents, hair growth promoters, analgesics, germicides, anti-inflammatory agents, refreshing agents, and skin anti-aging agents, but are not limited thereto.

The external use preparation is a product to be applied to human skin, nails, hair, and the like and, for example, medicament active components can be compounded therein and used in the treatment of various disorders. The cosmetic composition is also a product to be applied to human skin, nails, hair, and the like, and is used for beauty purposes. The external use preparation or cosmetic composition is preferably an anti-perspirant, a skin cleansing agent, a skin conditioner, a skin cosmetic composition product, a hair cleansing agent, an external use preparation for hair or a hair cosmetic composition.

An antiperspirant, skin cleansing agent, skin external use preparation, or skin cosmetic composition pertaining to the present invention contains a glycerin derivative-modified silicone composition obtained by the production method of the present invention, and the form thereof is not particularly limited, but may be in the form of a solution, milk-like, cream-like, solid, semi-solid, paste-like, gel-like, powder-like, multi-layer, mousse-like, or a water-in-oil or oil-in-water emulsion composition. Specific examples of the skin external use preparation or the skin cosmetic composition product according to the present invention include toilet water, emulsions, creams, sunscreen emulsions, sunscreen creams, hand creams, cleansing compositions, massage lotions, cleansing agents, anti-perspirants, deodorants, and similar basic cosmetic products; foundations, make-up bases, blushers, rouges, eye shadows, eye liners, mascaras, nail enamels, and similar make-up cosmetic products; and the like.

Similarly, a hair cleansing agent, hair external use preparation or the hair cosmetic composition product pertaining to the present invention contains a glycerin derivative-modified silicone composition obtained by the production method of the present invention and can be used in various forms. For example, the hair cleansing agent, the hair external use preparation or the hair cosmetic composition product according to the present invention may be dissolved or dispersed in an alcohol, a hydrocarbon, a volatile cyclic silicone, or the like and used; furthermore, these may be used in the form of an emulsion by dispersing a desired emulsifier in water. Additionally, the hair cleansing agent, the hair external use preparation or the hair cosmetic composition product according to the present invention can be used as a spray by using propane, butane, trichloromonofluoromethane, dichlorodifluoromethane, dichlorotetrafluoroethane, carbonic acid gas, nitrogen gas, or a similar propellant. Examples of other forms include milk-like, cream-like, solid, semi-solid, paste-like, gel-like, powder-like, multi-layer, mousse-like, and similar forms. There various forms can be used as shampooing agents, rinsing agents, conditioning agents, setting lotions, hair sprays, permanent wave agents, mousses, hair colorants, and the like.

In addition, the type, form, and container of the cosmetic or external use preparation composition according to the present invention are the same as those disclosed in paragraphs 0230 to 0233 and the like of Patent Document 11.

The following other components generally used in external use preparations or cosmetic compositions may be added to the external use preparation or the cosmetic composition of the present invention, provided that such components do not inhibit the effectiveness of the present invention: water, powders or coloring agents, alcohols, water-soluble polymers, film-forming agents, oil agents, oil-soluble gelling agents, organo-modified clay minerals, surfactants, resins, UV absorbers, salts, moisturizing agents, preservatives, antimicrobial agents, perfumes, salts, antioxidants, pH adjusting agents, chelating agents, refreshing agents, anti-inflammatory agents, skin beautifying components (skin-lightening agents, cell activating agents, agents for ameliorating skin roughness, circulation promoters, astringents, antiseborrheic agents, and the like), vitamins, amino acids, nucleic acids, hormones, clathrates, and the like; bioactive substances, medicament active ingredients, and perfumes. However, the additives are not particularly limited to thereto.

The water that can be used in the cosmetic or external use preparation of the present invention needs to be clean and free of components that are harmful to the human body, and examples thereof include tap water, purified water, mineral water, and deep sea water.

(Oil Agent)

The oil agent that can be used in the cosmetic or external use preparation according to the present invention is preferably one or more oil agents selected from silicone oils, non-polar organic compounds, and lowly polar to highly polar organic compounds that are liquid at 5 to 100° C., and the non-polar organic compounds and lowly polar to highly polar organic compounds are preferably hydrocarbon oils, fatty acid ester oils, and liquid fatty acid triglycerides. These are components that are particularly widely used as base materials for cosmetic compositions, but it is possible to additionally use one or more types of compound selected from among publicly known vegetable oils and fats, animal oils and fats, higher alcohols, fatty acid triglycerides, artificial sebum and fluorine-based oils as well as these oil agents.

By combining the hydrocarbon oil and/or the fatty acid ester oil with the silicone oil, in addition to the dry tactile sensation unique to silicone oils, moisture will be retained on the skin and a moisturizing feel whereby the skin or hair feels moisturized (also referred to as a luxurious tactile sensation) and smooth tactile sensation can be imparted to the cosmetic composition of the present invention. Moreover, there is a benefit in that stability over time of the cosmetic composition will not be negatively affected. Furthermore, with a cosmetic composition comprising the hydrocarbon oil and/or the fatty acid ester oil and the silicone oil, these moisturizing components (the hydrocarbon oil and/or the fatty acid ester oil) can be applied on the skin or hair in a more stable and uniform manner. Therefore, the moisturizing effects of the moisturizing components on the skin are improved. Thus, compared to a cosmetic composition comprising only a non silicone-based oil agent (e.g. a hydrocarbon oil, a fatty acid ester oil, or the like), the cosmetic composition comprising a non silicone-based oil agent along with a silicone oil is advantageous in that a smoother, more luxurious tactile sensation is imparted.

These oil agents are the same as those disclosed in paragraphs 0130 to 0135, paragraph 0206, and the like of Patent Document 11. Examples of the fluorine-based oil include perfluoropolyether, perfluorodecalin, perfluorooctane, and the like.

(Powder or Coloring Agent)

A powder or coloring agent which can be used in the cosmetic or external use preparation according to the present invention is one that is commonly used as a component of a cosmetic composition, and includes white or colored pigments and extender pigments. The white and colored pigments are used to impart color and the like to the cosmetic composition, and the extender pigments are used to improve the tactile sensation and the like of the cosmetic composition. In the present invention, white and colored pigments as well as extender pigments commonly used in cosmetic compositions can be used as the powder without any particular restriction. In the present invention, preferably, one or two or more of the powders are compounded. The form (sphere, bar, needle, plate, amorphous, spindle, cocoon, or the like), particle size (aerosol, micro-particle, pigment-grade particle, or the like), and particle structure (porous, nonporous, or the like) of the powder are not limited in any way, but an average primary particle size is preferably in a range of 1 nm to 100 µm. Particularly, when compounding the powder or coloring agent as a pigment, preferably one or two or more selected from an inorganic pigment powder, an organic pigment powder, and a resin powder having an average diameter in a range of 1 nm to 20 µm is compounded.

Examples of the powder include inorganic powders, organic powders, surfactant metal salt powders (metallic soaps), colored pigments, pearl pigments, metal powder pigments, and the like. Compounded products of these pigments can be used. Furthermore, the surfaces of these pigments may be water-repellent treated.

Specific examples include the same powders or colorants disclosed in paragraphs 0150 to 0152 or the like of Patent Document 11.

Of the powders recited, description of a silicone elastomer powder shall be given. The silicone elastomer powder is a crosslinked product of a straight diorganopolysiloxane formed principally from diorganosiloxy units (D units), and can be preferably obtained by crosslinking an organohydrogenpolysiloxane having a silicon-bonded hydrogen atom on the sidechain or the molecular terminal and a diorganopolysiloxane having an unsaturated hydrocarbon group such as an alkenyl group or the like on the sidechain or the molecular terminal, in the presence of a hydrosilylation reaction catalyst. Compared to a silicone resin powder formed from T units and Q units, the silicone elastomer powder is soft, has elasticity, and has superior oil absorbency. Therefore, oils and fats on the skin can be absorbed and makeup smearing can be prevented. When surface treatment is performed on the glycerin derivative-modified silicone composition obtained by the production method of the present invention, uniform treatment can be performed with good treatment efficiency, and thus it is possible to provide a unique effect or feel corresponding to the type of the glycerin derivative-modified silicone without diminishing the suede-like feel of the silicone elastomer powder. Furthermore, when the glycerin derivative-modified silicone composition is blended into a cosmetic together with a silicone elastomer powder, the dispersion stability of the powder in the overall cosmetic composition is improved, and it is possible to obtain a cosmetic that is stable over time.

The silicone elastomer powder can be in various forms such as spherical, flat, amorphous, or the like. The silicone elastomer powder may also be in the form of an oil dispersion. With the cosmetic composition of the present invention, the silicone elastomer powder is particulate in form, and the primary particle size observed using an electron microscope and/or the average primary particle size measured by laser analysis or scattering is in a range of 0.1 to 50 µm. Additionally, a silicone elastomer powder having spherical primary particles can be preferably compounded. The silicone elastomer that constitutes the silicone elastomer powder is preferably one having a hardness, as measured using a type A durometer in the "Rubber, Vulcanized or Thermoplastic—Determination of Hardness" specified in JIS K 6253, of 80 or lower, and more preferably 65 or lower.

Of these silicone elastomer powders, specific examples of silicone elastomer spherical powders, in particular, are the same as those disclosed in paragraph 0168 of Patent Document 11 and may be silicone elastomer powders that have been subjected to various surface treatments such as water-repellent treatment, as disclosed in paragraphs 0150 to 0152.

It is possible to further blend another surfactant in the cosmetic or external use preparation of the present invention. These other surfactants are components that function as cleansing components of the skin or the hair or, alternatively, as the oil agent or an emulsifier, and can be selected as desired depending on the type and function of the cosmetic composition. More specifically, the other surfactants can be selected from the group consisting of an anionic surfactant, a cationic surfactant, a nonionic surfactant, an amphoteric surfactant, and a semipolar surfactant. Preferably a silicone-based nonionic surfactant is used in combination.

These surfactants are the same as those disclosed in paragraphs 0162, 0163, 0195 to 0201, and the like of Patent Document 11. The glycerin derivative-modified silicone pertaining to the present invention functions as a dispersant because it has polar groups and non-polar groups in the molecule. Therefore, when used in combination with a nonionic surfactant, it functions as an aid to enhance the stability of the nonionic surfactant, and may improve the overall stability of the formulation. In particular, the glycerin derivative-modified silicone composition obtained by the production method of the present invention can be used in combination with a polyoxyalkylene-modified silicone, a polyglyceryl-modified silicone, a glyceryl-modified silicone, a sugar-modified silicone, and a sugar alcohol-modified silicone due to its enhanced compatibility and affinity with various modified silicones. Moreover, nonionic surfactants of these silicones in which an alkyl branch, a straight chain silicone branch, a siloxane dendrimer branch, or the like is provided as necessary along with the hydrophilic group can also be advantageously used.

Depending on the intended use thereof, the cosmetic or external use preparation of the present invention can contain one or two or more polyhydric alcohols and/or lower monohydric alcohols. These alcohols are the same as those disclosed in paragraphs 0159, 0160, and the like of Patent Document 11.

Depending on the purpose thereof, the cosmetic or the external use preparation of the present invention can contain one or two or more inorganic salts and/or organic salts. These salts are the same as those disclosed in paragraph 0161 and the like of Patent Document 11.

Depending on the purpose thereof, the cosmetic or the external use preparation of the present invention can contain at least one selected from the group consisting of a crosslinking organopolysiloxane, an organopolysiloxane elastomer spherical powder, a silicone resin, an acryl silicone dendrimer copolymer, a silicone raw rubber, a polyamide-modified silicone, an alkyl-modified silicone wax, and an alkyl-modified silicone resin wax. These silicone-based components are the same as those disclosed in paragraphs 0162 to 0194 and the like of Patent Document 11.

Depending on the intended use thereof, the cosmetic or external use preparation of the present invention can contain one or two or more water-soluble polymers. These water-soluble polymers are the same as those disclosed in paragraph 0201 and the like of Patent Document 11.

Depending on the intended use thereof, the cosmetic or external use preparation of the present invention can contain one or two or more ultraviolet light blocking components. These ultraviolet light blocking components are the same as the organic and inorganic ultraviolet light blocking components disclosed in paragraphs 0202 to 0204 and the like of Patent Document 11, but specifically, an ultraviolet light blocking component that can be suitably used is at least one selected from the group consisting of microparticulate titanium oxide, microparticulate zinc oxide, 2-ethylhexyl p-methoxycinnamate, 4-tert-butyl-4'-methoxydibenzoylmethane, diethylamino hydroxybenzoyl hexyl benzoate, benzotriazole-based UV absorbers, and triazine-based UV absorbers such as 2,4,6-tris[4-(2-ethylhexyloxycarbonyl)anilino]1,3,5-triazine (INCI: octyl triazone) and 2,4-bis([4-(2-ethyl-hexyloxy)-2-hydroxy]phenyl)-6-(4-methoxyphenyl)-1,3,5-triazine (INCI: bis-ethylhexyloxyphenol methoxyphenyl triazine, trade designation: Tinosorb®S). These ultraviolet light blocking components are generally used, are easy to acquire, and have high ultraviolet light blocking effects and, thus can be beneficially used. In particular, using both inorganic and organic ultraviolet light blocking components is preferable, and using a UV-A blocking component in combination with a UV-B blocking component is more preferable.

By using an ultraviolet light blocking component in combination with the glycerin derivative-modified silicone composition in the cosmetic or the external use preparation of the present invention, it is possible to stably disperse the ultraviolet light blocking component in the cosmetic composition while improving the feeling to touch and storage stability of the overall cosmetic composition, and it is therefore possible to impart excellent ultraviolet light blocking properties to the cosmetic composition.

Various components other than the components described above can be used in the cosmetic composition or external use preparation of the present invention, provided that such use does not impair the effects of the present invention. Examples thereof include oil-soluble gelling agents, organo-modified clay minerals, preservatives, bioactive components, skin beautifying components, pH adjusting agents, antioxidants, solvents, chelating agents, moisturizing components, perfumes and the like. These optional components for a cosmetic product are the same as those disclosed in paragraphs 0207, 0208, 0220 to 0228, and the like of Patent Document 11.

Additionally, in cases where the external use preparation or the cosmetic composition according to the present invention is an anti-perspirant, or depending on the purpose thereof, the external use preparation or the cosmetic composition can contain an anti-perspiration active component and/or a deodorant agent. These antiperspiration components and deodorant components are the same as those disclosed in paragraphs 0209 to 0219 and the like of Patent Document 11. Similarly, in cases in which the cosmetic or external use preparation according to the present invention is an antiperspirant composition, the preparation, method of use, and the like of the various antiperspirant compositions are the same as those disclosed in paragraphs 0234 to 0275 and the like of Patent Document 11.

INDUSTRIAL APPLICABILITY

The production method for a glycerin derivative-modified silicone composition of the present invention is inexpensive and simple, produces little waste, has excellent yield or productivity, and can reasonably accommodate production on a commercial scale. Furthermore, the glycerin derivative-modified silicone composition obtained by the production method of the present invention has extremely low risk of phase separation or sedimentation of unreacted starting materials or the like after production. In particular, because the glycerin derivative-modified silicone composition obtained by the production method of the present invention maintains a highly transparent appearance and constant viscosity regardless of the temperature environment used, there are no problems arising from an opaque appearance, and ease of handling is excellent. Therefore, the present invention solves the fundamental problems of conventional glycerin-modified silicone.

Therefore, the glycerin derivative-modified silicone composition of the present invention not only can be used in cosmetics or external use preparations such as medicaments, but can also be widely used in general industrial applications, and can provide the above various applications with the emulsification/dispersion effect, surface treatment effect, adsorption effect, coating effect, moisture retention/water retention effect, emollient effect, abrasion reduction effect, lubrication effect, penetrating capability, solubilizing/compatibilizing capability, protection effect, adhesion effect, viscosity-increasing or viscosity-adjusting effect, or maintenance of these effects, and the like that are intrinsic to glycerin derivative-modified silicone.

Specifically, the glycerin derivative-modified silicone composition obtained by the production method of the present invention can be suitably used not only as a raw material for external use preparations, medicaments, or cosmetics, but also, for example, as a fiber treating agent, a varnish or paint additive with excellent heat resistance, weather resistance, and electrical characteristics, a coating agent, a primer, a tackifier, a polyol main agent, a foam stabilizer, or a modifier for various urethanes or foaming materials, a mold-releasing agent or peeling agent, an antifoam agent, greases or oil compounds, oils for insulation, burnishing, water repellency, heating/cooling mediums, lubrication, or the like, a modifier, additive, or surface treating agent for a rubber or resin, a compounding agent, modifier, or precursor for a silane coupling agent, a coating material or sealing material for a building/lining, a protecting agent or lubricant or buffering agent for optical fibers/electrical lines, and raw materials for general industrial materials such as electronic/electrical parts.

EXAMPLES

The present invention will be described in detail hereinafter using working examples and comparative examples, but the present invention is not limited to the working examples described below.

Note that in the working examples and comparative examples below, the language "production of glycerin derivative-modified silicone no. X" is used for the sake of convenience, but the obtained products are in the form of mixtures containing a small amount of unreacted starting material and the like in addition to the main components. The viscosity of the samples is the viscosity (mPa·s) at 25° C. measured by an E-type rotating viscometer. Light transmittance of each of the obtained samples was measured at room temperature (25° C.) by the method described below.

[Light Transmittance]

The light transmittance (%) at a wavelength of 750 nm and a cell thickness of 10 mm was measured using a light transmittance meter [manufactured by the Shimadzu Corporation, UV-265FW]. Purified water was used as a control.

In the following compositional formulae, "Me" represents a methyl (—$CH_3$) group, "M" represents a $Me_3SiO$ group (or an $Me_3Si$ group), "D" represents an $Me_2SiO$ group, "$D^H$" represents an MeHSiO group, and "$M^R$" and "$D^R$" respectively represent units in which a methyl group in "M" or "D" is modified by any substituent. Additionally, in the production examples, "IPA" represents isopropyl alcohol.

Production Example 1

<Synthesis of Glycerin Derivative-Modified Silicone No. 1>

Step 1: First, 401.1 g of methylhydrogenpolysiloxane represented by the average composition formula $MD_{43.4}D^H{}_{7.4}M$, 3.5 g of vinyl tris(trimethylsiloxy)silane represented by the average composition formula $CH_2=CH—Si(OSiMe_3)_3$, and 75.0 g of hexadecene (α-olefin purity=91.7%) (first time) were put into a reaction vessel and heated while stirring under a nitrogen stream. Then, 0.4 mL of a hexamethyldisiloxane solution of platinum-1,3-divinyl-1,1,3,3-tetramethyldisiloxane complex (Pt concentration 0.45 wt. %) was added, and a reaction was performed for 1 hour at 55 to 75° C. The reaction liquid was collected, and when confirmed by an alkali decomposition gas generation method (the remaining Si—H groups are decomposed using a KOH ethanol/water solution, and the reaction rate is calculated from the volume of the produced hydrogen gas), the reaction rate was as planned.

Step 2: Next, 45.7 g of diglycerin monoallyl ether, 0.07 g of natural vitamin E, and 340 g of IPA were added to the reaction liquid, and 0.67 mL of the same platinum catalyst solution as described above was further added. A reaction was performed for 2.5 hours at 45 to 60° C., and when confirmed by the same method, the reaction rate was as planned.

Step 3: Then, 75.1 g of hexadecene (α-olefin purity=91.7%) (second time) was put into the reaction liquid, and 0.27 mL of the same platinum catalyst solution as described above was further added. A reaction was performed for 1.5 hours at 50 to 60° C., and when confirmed by the same method, the reaction was complete. Then, the reaction liquid was heated under reduced pressure to distill out the low-boiling components.

Step 4: An aqueous solution in which 0.09 g of sodium hydrogen sulfate-hydrate was dissolved in 7.5 g of purified water was added to the contents of the reaction vessel, and acid treatment was performed for 20 minutes at 70 to 80° C. while stirring under a nitrogen stream. Then, the pressure was reduced at 70° C., and when water and other low-boiling components stopped distilling out, the pressure was recovered (first acid treatment). Next, 7.5 g of water was added and the same treatment was performed, and then, when water and other low-boiling components stopped distilling out, the pressure was recovered (second acid treatment). The same operations were repeated, and the state of heating under reduced pressure was maintained for 1 hour after water and other low-boiling components stopped distilling out, and after the water droplets in the system disappeared, the pressure was recovered (third acid treatment).

Step 5: An aqueous solution in which 0.06 g of sodium bicarbonate was dissolved in 3 g of purified water was added to the contents of the reaction vessel, and neutralizing treatment was performed for 30 minutes at 60 to 70° C. while stirring under a nitrogen stream. Then, the pressure was reduced at 70° C., and the state of heating under reduced pressure was maintained for 1 hour after water and other low-boiling components stopped distilling out, and after the water droplets in the system disappeared, the pressure was recovered. As a result, 597 g of a composition containing the glycerin derivative-modified silicone represented by the average composition formula $MD_{43.4}D^{R*11}{}_{4.91}D^{R*31}{}_{0.1}D^{R*21}{}_{2.07}D^{OR}{}_{0.32}M$ was obtained as a grayish brown opaque uniform liquid. (Yield=100×597/600=99.5%)

Here, $R^*{}_{11}$, $R^{*21}$, and $R^{*31}$ are as follows. Also, $D^{OR}$ is a structural unit produced by a dehydrogenation reaction of $D^H$ and an alcoholic hydroxyl group or water component, and is an Me(OR)SiO group containing an Si—O—C bond or Si—O—H bond.

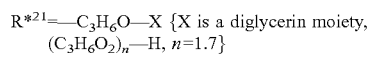

Comparative Example 1

<Comparative Composition RE-1 Containing Glycerin Derivative-Modified Silicone No. 1>

The grayish brown opaque uniform liquid obtained in Production Example 1 (reaction mixture containing glycerin derivative-modified silicone as the main component) was used as a sample without further changes.

Comparative Example 2

<Preparation of Comparative Composition RE-2 Containing Glycerin Derivative-Modified Silicone No. 1>

When 500 g of the grayish brown opaque uniform liquid obtained in Production Example 1 was filtered (two passes)

with a pressure filter at room temperature using 10 g of Hiflo Super Cell (Celite Corporation, flux calcined diatomaceous earth) as a filter aid and using ADVANTEC No. 424 (diameter: 110 mm, Toyo Roshi Co., Ltd.) as filter paper, 471 g of a grayish brown opaque uniform liquid was obtained. (Yield=99.5×471/500=93.7%) The transparency of the appearance of this composition was not improved whatsoever in comparison to the composition obtained in Production Example 1 (Comparative Example 1).

Comparative Example 3

Preparation of Comparative Composition RE-3 Containing Glycerin Derivative-Modified Silicone No. 1>
Next, 9 g of Shirasagi WH2C20/48SS (Japan Enviro-Chemicals, Limited, activated carbon) as an adsorbent was mixed with 455 g of the grayish brown opaque uniform liquid obtained in Comparative Example 2, and when pressure filtration (two passes) was performed at room temperature using the filter layer formed in Comparative Example 2, 445 g of grayish brown opaque uniform liquid was obtained. (Yield≈99.5×445/455=97.3%) The transparency of appearance of this composition was not improved whatsoever in comparison to the composition obtained in Production Example 1 (Comparative Example 1).

Comparative Example 4

<Preparation of Comparative Composition RE-4 Containing Glycerin Derivative-Modified Silicone No. 1>
Next, 430 g of the grayish brown opaque uniform liquid obtained in Comparative Example 3 was pressure-filtered (two passes) using a specialized cartridge filter with a Zeta Plus Filter 30C (diameter: 90 mm, 3M Corporation, zeta-potential adsorption filter). At that time, since filtration was extremely slow at room temperature, it was performed while maintain the temperature at 40 to 50° C., and even still, the filtration speed was considerably slower compared to Comparative Examples 2 and 3. The first approximately 50 g of the filtrate of the first pass had an improved semi-transparent appearance, but cloudiness appeared thereafter. Therefore, the composition was mixed so that the entire amount of the filtrate that was ultimately obtained was uniform, and as a result, 393 g of a grayish pale brown opaque uniform liquid was obtained. (Yield≈99.5×393/430=90.9%) The transparency of appearance of this composition was slightly improved in comparison to the composition obtained in Production Example 1 (Comparative Example 1).

Comparative Example 5

<Preparation of Comparative Composition RE-5 Containing Glycerin Derivative-Modified Silicone No. 1>
Next, 3.8 g of Kyoward 600S and 3.8 g of Kyoward 500SH (Kyowa Chemical Industry Co., Ltd., synthetic hydrotalcite adsorbents) were mixed with 380 g of the grayish pale brown opaque uniform solution obtained in Comparative Example 4, and pressure filtration in the same manner was attempted using the filter layer formed in Comparative Example 3. Incidentally, because almost no filtrate was obtained at room temperature, the filter was transferred to an oven and filtration was performed while heating at 60 to 70° C. However, due to clogging by the Kyoward, the recovered amount of filtrate did not go beyond approximately 100 g (grayish pale brown semi-transparent cloudy liquid), and therefore the second pass could not be performed. (Yield<99.5×100/380=26.2%)

Working Example 1

<Preparation of Working Example Composition 1 Containing Glycerin Derivative-Modified Silicone No. 1>
First, 24.0475 g of the grayish brown opaque uniform liquid obtained in Production Example 1 (reaction mixture containing glycerin derivative-modified silicone as the main component) was collected in a 35 mL glass bottle, and 0.3679 g of purified water (equivalent to 1.53 wt. % relative to the reaction mixture) was added. When homogenization was attempted by stirring the entirety well with a stainless steel spatula for approximately 5 minutes, it was unexpectedly discovered that a nearly transparent pale brown uniform liquid was produced.

Working Example 2

<Preparation of Working Example Composition 2 Containing Glycerin Derivative-Modified Silicone No. 1>
First, 12.2 g of the nearly transparent pale brown uniform liquid obtained in Working Example 1 was collected in a 35 mL glass bottle, and 12.2 g of FZ-3196 (Dow Corning Toray Co., Ltd., caprylyl methicone) was added (equivalent to 100 wt. % relative to working example composition 1). When homogenization of the entirety was attempted by shaking, it was unexpectedly discovered that a low-viscosity slightly brown nearly transparent uniform liquid was produced.

Comparative Example 6

<Preparation of Comparative Composition RE-6 Containing Glycerin Derivative-Modified Silicone No. 1>
First, 24.0118 g of the grayish brown opaque uniform liquid obtained in Production Example 1 (reaction mixture containing glycerin derivative-modified silicone as the main component) was collected in a 35 mL glass bottle, and a small amount of 1,3-butylene glycol was added, and homogenization was attempted by stirring the entirety well with a stainless steel spatula. It was mixed under conditions such that the added amount of 1,3-butylene glycol was 1.0 wt. %, 1.5 wt. %, 2.0 wt. %, 3.0 wt. %, 4.1 wt. %, 5.1 wt. %, 6.2 wt. %, 7.2 wt. %, 8.2 wt. %, and 10.1 wt. % relative to the reaction mixture, but the cloudiness of appearance was not improved. Furthermore, for comparison with Working Example 1, the mixture in which the added amount of 1,3-butylene glycol was 1.5 wt. % was used as comparative example composition RE-6.

Comparative Example 7

<Preparation of Comparative Composition RE-7 Containing Glycerin Derivative-Modified Silicone No. 1>
First, 12.4 g of the grayish brown opaque uniform liquid obtained in Production Example 1 (reaction mixture containing glycerin derivative-modified silicone as the main component) was collected in a 35 mL glass bottle, and 12.4 g of FZ-3196 (Dow Corning Toray Co., Ltd., caprylyl methicone) (equivalent to 100 wt. % relative to the above working example composition 1) was added. When homogenization of the entirety was attempted by shaking, a low-viscosity grayish brown opaque uniform liquid was obtained.

The details of the "working example compositions 1 and 2 containing glycerin derivative-modified silicone No. 1,"

which are the stabilized compositions containing glycerin derivative-modified silicone pertaining to the present invention, and "comparative compositions RE-1 to RE-7 containing glycerin derivative-modified silicone No. 1" pertaining to the comparative examples prepared by the methods described above are shown in the following Tables 1 and 2.

TABLE 1

| | Appearance | Dilute oil agent | Loss %*1) | Chemical structure of main component*2) |
|---|---|---|---|---|
| Working Example 1 | Nearly transparent uniform liquid | None | ~0.5 | $MD_{43.4}D^{R*11}{}_{4.91}D^{R*31}{}_{0.1}D^{R*21}{}_{2.07}D^{OR}{}_{0.32}M$ |
| Working Example 2 | Nearly transparent uniform liquid | FZ-3196 | ~0.5 | |
| Comparative Example 1 | Opaque uniform liquid | None | 0.5 | |
| Comparative Example 2 | Opaque uniform liquid | None | 6.3 | |
| Comparative Example 3 | Opaque uniform liquid | None | 2.7 | |
| Comparative Example 4 | Opaque uniform liquid | None | 9.1 | |
| Comparative Example 5 | Semi-transparent cloudy liquid | None | >73.8 | |
| Comparative Example 6 | Opaque non-uniform liquid | None | ~0.5 | |
| Comparative Example 7 | Opaque uniform liquid | FZ-3196 | ~0.5 | |

Note*1)
Calculated as loss % = (100 − yield) %; serves as a measure of the amount of waste produced.
Note*2)
The chemical structure of the glycerin derivative-modified silicone serving as the main component is represented by an average composition formula.

In the table, the structures and types of the functional groups are as follows. Furthermore, $D^{OR}$ is a structural unit produced by a dehydrogenation reaction of $D^H$ and an alcoholic hydroxyl group or water component, and is an Me(OR)SiO group containing an Si—O—C bond or Si—O—H bond.

<Group Having a Siloxane Dendron Structure: $R^{*3}$>

$R^*{}_{31}$=—$C_2H_4Si(OSiMe_3)_3$

<Glycerin Derivative Group: $R^{*2}$>

$R^{*21}$=—$C_3H_6O$—X {X is a diglycerin moiety $(C_3H_6O_2)_n$—H, n=1.7}

<Other Organic Groups: $R^{*1}$>

$R^{*11}$=—$C_{16}H_{33}$

TABLE 2

| | Concentration*3) | Light transmittance*4) | Viscosity*5) | Filtration time*6) |
|---|---|---|---|---|
| Working Example 1 | 98.6 | 83.4 | 2440 | 0 (unnecessary) |
| Working Example 2 | 49.3 | 88.2 | 104 | 0 (unnecessary) |
| Comparative Example 1 | 100 | 0.3 | 1340 | 0 (not performed) |
| Comparative Example 2 | 100 | 0.3 | — | 2 |
| Comparative Example 3 | 100 | 0.3 | — | 2 |
| Comparative Example 4 | 100 | 1.2 | — | 5 |
| Comparative Example 5 | 100 | NA*7) | — | 8 |
| Comparative Example 6 | 98.5 | 0.2 | — | 0 (not performed) |
| Comparative Example 7 | 49.3 | 0.5 | 81 | 0 (not performed) |

Note*3)
Expresses the concentration (wt. %) of reaction mixture containing glycerin derivative-modified silicone as the main component in the sample.
Note*4)
Expresses the light transmittance T % of the sample at room temperature (wavelength: 750 nm, cell thickness: 10 mm).
Note*5)
Value of the viscosity (mP · s) of the sample at 25° C.; expressed as a numerical value measured with an E-type rotary viscometer.
Note*6)
Expresses the time (hours) required to filter during sample preparation; serves as a measure of production efficiency.
Note*7)
In the production method of Comparative Example 5, the entire amount of composition could not be filtered, and since the small amount of obtained filtrate did not represent the appearance of the overall composition, light transmittance was not measured.

[Stability Test 1]

First, 12 g of each of the samples of Working examples 1 and 2 and Comparative Examples 1 and 7 was placed in a 35 mL glass vial and stopped tightly. These were placed in a thermostatic bath at 50° C. and left for one month. Then, after the appearance of each of the samples at 50° C. was observed, they were removed from the thermostatic bath and returned to room temperature. The appearance of each of the samples was observed, and light transmittance and viscosity were measured. The results are shown in Table 3.

TABLE 3

| | Appearance (50° C.) | Appearance (room temperature) | Light transmittance (room temperature)*8) | Viscosity (25° C.) {Rate of change %}*9) |
|---|---|---|---|---|
| Working Example 1 | Semi-transparent uniform liquid | Nearly transparent uniform liquid | 92.0 | 0 |
| Working Example 2 | Semi-transparent or transparent liquid | Nearly transparent uniform liquid | 98.4 | −8.0 |
| Comparative Example 1 | Opaque uniform liquid | Opaque uniform liquid | 1.5 | −3.0 |
| Comparative Example 7 | Obvious phase separation into transparent liquid (top) and cloudy liquid (bottom) | Semi-transparent cloudy liquid (top) and opaque viscous sediment | — | — |

Note*8)
Expresses the light transmittance T % of the sample at room temperature (wavelength: 750 nm, cell thickness: 10 mm).
Note*9)
Expresses the rate of change % in viscosity from the initial value.

[Stability Test 2]

First, 12 g of each of the samples of Working examples 1 and 2 and Comparative Examples 1 and 7 was placed in a 35 mL glass vial and stopped tightly. These were placed in a refrigerator at −5° C. and left for one month. Then, after the appearance of each of the samples at −5° C. was observed, they were removed from the refrigerator and returned to room temperature. The appearance of each of the samples was observed, and light transmittance and viscosity were measured. However, after being returned to room temperature, there were many samples in which slight phase separation was seen in the appearance. Therefore, all samples were homogenized by mixing for approximately 1 to 3 minutes with a stainless steel spatula, and then light transmittance and viscosity were measured. The results are shown in Table 4.

TABLE 4

|  | Appearance (−5° C.) | Appearance (room temperature) | Light transmittance (room temperature)*8) | Viscosity (25° C.) {Rate of change %}*9) |
|---|---|---|---|---|
| Working Example 1 | Opaque Solid | Transparent uniform liquid (top) and semi-transparent sedimented oil*10) | 73.4 | 0 |
| Working Example 2 | Transparent uniform liquid | Nearly transparent uniform liquid | 72.2 | −3.1 |
| Comparative Example 1 | Opaque Solid | Opaque liquid (top) and opaque viscous sediment | 0.2 | +5.0 |
| Comparative Example 7 | Opaque uniform liquid | Opaque liquid (top) and opaque viscous sediment | 0.3 | +0.7 |

Note*8)
Expresses the light transmittance T % of the sample at room temperature (wavelength: 750 nm, cell thickness: 10 mm).
Note*9)
Expresses the rate of change % in viscosity from the initial value.
Note*10)
Except for the samples of Comparative Examples 1 and 7, affinity between the separated top phase and bottom phase was good and fluidity characteristics were close, and they were easily returned to nearly uniform semi-transparent or transparent liquids by lightly stirring. On the other hand, miscibility between the top phase and the sediment of both comparative examples was poor and there were differences in fluidity, and time was required to homogenize by stirring.

From the above results it was confirmed that the samples of the working examples had far superior homogeneity and transparency of appearance than the samples of the comparative examples, and this superiority was unchanged at high temperature and low temperature.

It was also ascertained that the viscosity of the samples of the working examples was stable within a fluctuation range of less than ±10% even after going through a high temperature and low temperature history, and there were no problems in practical use.

Hereinafter, formulation examples of the cosmetic composition and the external use preparation according to the present invention are described, but the cosmetic composition and the external use preparation according to the present invention are not limited to the types and compositions recited in these formulation examples.

The stabilized composition containing the glycerin derivative-modified silicone pertaining to the present invention may be used in various external use preparations and cosmetics. Specific formulation examples thereof are compositions in which components corresponding to silicone compound Nos. 1 to 16 in Formulation Examples 1 to 43 of various cosmetics and external use preparations described in Patent Document 11 (WO/2011/049248) and/or various polyether-modified silicones are substituted with the stabilized composition containing glycerin derivative-modified silicone pertaining to the present invention (working example compositions 1 and 2 containing glycerin derivative-modified silicone No. 1).

Further examples are compositions in which components corresponding to silicone compound Nos. 1 to 14 in Formulation Examples 1 to 24 of various cosmetics and external use preparations described in Patent Document 12 (WO/2011/049247) and/or various polyether-modified silicones are substituted with the stabilized composition containing glycerin derivative-modified silicone pertaining to the present invention (working example compositions 1 and 2 containing glycerin derivative-modified silicone No. 1).

Further examples are compositions in which components corresponding to AB-type organopolysiloxane copolymers P1 to P6 contained in Formulation Examples 1 to 10 of various cosmetics and external use preparations (Synthesis Examples 1 to 12) described in Patent Document 13 (WO/2011/049246) and/or various polyether-modified silicones are substituted with the stabilized composition containing glycerin derivative-modified silicone pertaining to the present invention (working example compositions 1 and 2 containing glycerin derivative-modified silicone No. 1).

Further examples are compositions in which components corresponding to silicone compound Nos. 1 to 8 in the Formulation Examples of various cosmetics and external use preparations described in Patent Document 14 (Japanese Unexamined Patent Application Publication No. 2012-046507A) and/or various polyether-modified silicones are substituted with the stabilized composition containing glycerin derivative-modified silicone pertaining to the present invention (working example compositions 1 and 2 containing glycerin derivative-modified silicone No. 1).

Other than these, for example, formulations having the following hydrocarbon-based cosmetic base materials as the main component are also possible using working example composition 1 containing glycerin derivative-modified silicone No. 1 of the present invention. Furthermore, PEG-free formulations are also possible by substituting the entire amount of the following polyether-modified silicones with working example composition 1. In the list below, "parts" indicates parts by (weight) mass.

Formulation Example: Liquid Foundation (W/O)

(Components)

| 1. | Isodecane | 20 parts |
|---|---|---|
| 2. | Isohexadecane | 10 parts |
| 3. | Isotridecyl isononanoate | 3 parts |
| 4. | Caprylic/capric triglyceride | 2 parts |
| 5. | Polyether-modified silicone (note 1) | 1.0 part |
| 6. | Working example composition 1 containing glycerin derivative-modified silicone No. 1 | 1.0 part |
| 7. | Organic modified clay mineral (Benton 38V) | 1.5 parts |
| 8. | Octyl methoxycinnamate | 5 parts |
| 9. | Octyl silane-treated titanium oxide | 8.5 parts |
| 10. | Octyl silane-treated iron oxide red | 0.4 parts |
| 11. | Octyl silane-treated iron oxide yellow | 1 part |
| 12. | Octyl silane-treated iron oxide black | 0.1 parts |
| 13. | Dimethicone, dimethicone crosspolymer (note 2) | 2 parts |
| 14. | Isododecane/(acrylate/polytrimethylsiloxy methacrylate) copolymer (note 3) | 1 part |
| 15. | Trimethylsiloxysilicate | 1 part |
| 16. | 1,3-butylene glycol | 5 parts |
| 17. | Glycerin | 3 parts |

| 18. | Sodium chloride | 0.5 parts |
| 19. | Preservative | as appropriate |
| 20. | Purified water | remainder |
| 21. | Fragrance | as appropriate |

Note 1:
ES-5300, Dow Corning Toray Co., Ltd.
Note 2:
DC9045, Dow Corning Corp.
Note 3:
FA-4002ID, Dow Corning Toray Co., Ltd.

(Production Method)
Step 1: Components 1, 2, 5, 6, 7, 8, 13, 14, and 15 are stirred to mix.
Step 2: Components 3, 4, and 9 to 12 are kneaded to mix with three rollers.
Step 3: The mixture of step 2 is added to the mixture obtained in step 1 while stirring, and they are further stirred to mix.
Step 4: The water phase in which components 16 to 21 were uniformly dissolved is added to the mixture obtained in step 3 and emulsified, and a container is filled with it to obtain a product.

The obtained W/O liquid foundation has no unpleasant odor, and when used, has excellent emulsification stability, water resistance, and cosmetic durability, and makes skin texture and wrinkles less noticeable, has a light feeling to touch, and has excellent adhesion.

The invention claimed is:

1. A method for producing a transparent or semi-transparent liquid uniform glycerin derivative-modified silicone composition, the method comprising a hydration step of adding water to an opaque liquid glycerin derivative-modified silicone or composition thereof, wherein from 0.1 to 10 parts by mass of water per 100 parts by mass of the opaque liquid glycerin derivative-modified silicone or composition thereof is added in the hydration step, and wherein the opaque liquid glycerin derivative-modified silicone is represented by the structural formula (1-1):

$$X-\underset{CH_3}{\underset{|}{Si}}-O-\left(\underset{CH_3}{\underset{|}{Si}}-O\right)_{n1}-\left(\underset{CH_3}{\underset{|}{Si}}-O\right)_{n2}-\left(\underset{CH_3}{\underset{|}{Si}}-O\right)_{n3}-\left(\underset{CH_3}{\underset{|}{Si}}-O\right)_{n4}-\underset{CH_3}{\underset{|}{Si}}-X \quad (1\text{-}1)$$

wherein
$R^2$ is $C_{9-60}$ monovalent hydrocarbon group,
$L^1$ is $-C_2H_4Si(OSiMe)_3$,
Q is a glycerin derivative group selected from the groups represented by the following formula (5-1)

$$\diagdown_{R^5}\diagup^O\diagdown\diagup^{OH}\diagdown\diagup^O\diagdown\diagup^{OH}\diagdown\diagup^{OH} \quad (5\text{-}1)$$

and formula (5-2)

$$\diagdown_{R^5}\diagup^O\diagdown\diagup^{OH}\diagup^O\diagdown\diagup^{HO}\diagup^{OH},\diagup^{OH} \quad (5\text{-}2)$$

wherein R5 is a divalent organic group that does not contain an oxyalkylene structure wherein an average value of the number of repetitions of the oxyalkylene unit is two or more,
X is a group selected from the group consisting of a methyl group, $R^2$, $L^1$, and Q,
wherein n1, n2, n3, and n4 are each independently greater than 0 and n1+n2+n3+n4 is a number in a range of greater than 50 to 1,000.

2. The production method according to claim 1, wherein, in the hydration step, from 0.2 to 5 parts by mass of water per 100 parts by mass of the opaque liquid glycerin derivative-modified silicone or composition thereof is added.

3. The production method according to claim 1, wherein, in the hydration step, the opaque liquid glycerin derivative-modified silicone or composition thereof and the water are mixed to homogenize.

4. The production method according to claim 1, wherein a light transmittance at 750 nm (optical path length 10 mm) of the transparent or semi-transparent liquid uniform glycerin derivative-modified silicone composition is not less than 50%.

5. The production method according to claim 1, wherein $R^2$ is a monovalent hydrocarbon group having from 9 to 60 carbon atoms.

6. The production method according to claim 1, further comprising, before or after or simultaneously with the hydration step, a liquid oil agent addition step of adding a liquid oil agent to the opaque liquid glycerin derivative-modified silicone or composition thereof and/or the transparent or semi-transparent liquid uniform glycerin derivative-modified silicone composition.

7. The production method according to claim 6, wherein the liquid oil agent has affinity with the liquid glycerin derivative-modified silicone.

8. The production method according to claim 6, wherein, in the liquid oil agent addition step, from 5 to 1000 parts by mass of the liquid oil agent per 100 parts by mass of the liquid glycerin derivative-modified silicone or composition thereof is added.

9. The production method according to claim 6, wherein, in the liquid oil agent addition step, the opaque liquid glycerin derivative-modified silicone or composition thereof and/or the transparent or semi-transparent liquid uniform glycerin derivative-modified silicone composition is mixed with the liquid oil agent to homogenize.

10. The production method according to claim 1, wherein the liquid glycerin derivative-modified silicone or composition thereof is treated with an acidic aqueous solution, and water and odor-causing substances produced by treatment with the acidic aqueous solution are removed by heating or depressurization.

11. A transparent or semi-transparent uniform liquid glycerin derivative-modified silicone composition obtained by the production method according to claim 1.

12. An external use preparation, cosmetic, or industrial material comprising the transparent or semi-transparent uniform liquid glycerin derivative-modified silicone composition according to claim 11.

13. The production method according to claim 1, further comprising, before and after and simultaneously with the hydration step, a liquid oil agent addition step of adding a liquid oil agent to the opaque liquid glycerin derivative-modified silicone or composition thereof and/or the transparent or semi-transparent liquid uniform glycerin derivative-modified silicone composition.

14. The production method according to claim 1, further comprising, before or after, and simultaneously, with the hydration step, a liquid oil agent addition step of adding a liquid oil agent to the opaque liquid glycerin derivative-modified silicone or composition thereof and/or the transparent or semi-transparent liquid uniform glycerin derivative-modified silicone composition.

15. The production method according to claim 1, wherein $R^2$ is a monovalent hydrocarbon group having from 9 to 30 carbon atoms.

* * * * *